(12) United States Patent
Alkmin et al.

(10) Patent No.: US 8,480,387 B2
(45) Date of Patent: Jul. 9, 2013

(54) APPARATUS FOR MAKING A FIBROUS ARTICLE HAVING A THREE DIMENSIONAL PROFILE

(75) Inventors: Marco Antonio Alkmin, São José dos Campos (BR); José Francisco Cau, São José dos Campos (BR); Jose Manoel Soares Coutinho, Quiririm (BR); Ivair Luiz Duarte, Jardim Flórida Jacarei (BR); Reinaldo Lourenço Faria, São José dos Campos (BR); Francisco J. V. Hernandez, São José dos Campos (BR); Francisco Antonio Rimoli, Mogi das Cruzes (BR); Francisco Savastano Neto, Taubaté (BR); Alexandre Teixeira Yamashita, São José dos Campos (BR)

(73) Assignee: Johnson & Johnson DO Brasil Industria E Comercio Produtos Para Saude Ltda. (BR)

( * ) Notice: Subject to any disclaimer, the term of this patent is extended or adjusted under 35 U.S.C. 154(b) by 359 days.

(21) Appl. No.: 12/855,183

(22) Filed: Aug. 12, 2010

(65) Prior Publication Data
US 2012/0040039 A1    Feb. 16, 2012

(51) Int. Cl.
*B29C 43/14*    (2006.01)
(52) U.S. Cl.
USPC ............. 425/80.1; 425/290; 425/335

(58) Field of Classification Search
USPC ................. 425/80.1, 81.1, 290, 335
See application file for complete search history.

(56) References Cited

U.S. PATENT DOCUMENTS

| 1,599,648 | A | 9/1926 | Cochran |
| 1,974,578 | A | 9/1934 | Medoff |
| 2,064,431 | A | 12/1936 | Jurgensen |
| 2,331,355 | A | 10/1943 | Strongson |
| 2,408,508 | A | 10/1946 | Canavan |
| 2,747,575 | A | 5/1956 | Mercer |
| 2,852,026 | A | 9/1958 | Karr |
| 2,928,394 | A | 3/1960 | Roberts |
| 2,973,760 | A | 3/1961 | Dudley |

(Continued)

FOREIGN PATENT DOCUMENTS

| DE | 2113508 A1 | 9/1972 |
| EP | 249405 A2 | 12/1987 |

(Continued)

OTHER PUBLICATIONS

European Search Report dated Oct. 18, 2011 for corresponding EPA No. 11177496.4.

*Primary Examiner* — James Mackey

(57) ABSTRACT

The present invention generally relates to a method and apparatus for a making a formed fibrous article and more specifically to method and apparatus for making a formed fibrous article useful as an absorbent core structure in a disposable sanitary article such as a sanitary napkin, panty liner, diaper or the like. The present invention also relates to a disposable sanitary article including a formed fibrous article according to the present invention as a core structure thereof.

23 Claims, 11 Drawing Sheets

U.S. PATENT DOCUMENTS

| | | | |
|---|---|---|---|
| 3,420,234 A | 1/1969 | Phelps | |
| 3,844,288 A | 10/1974 | Kiela | |
| 3,897,784 A | 8/1975 | Fitzgerald | |
| 3,905,372 A | 9/1975 | Denkinger | |
| 3,906,952 A | 9/1975 | Zamist | |
| 4,046,147 A | 9/1977 | Berg | |
| 4,079,739 A | 3/1978 | Whitehead | |
| 4,490,147 A | 12/1984 | Pierce et al. | |
| 4,631,062 A | 12/1986 | Lassen et al. | |
| 4,666,440 A | 5/1987 | Malfitano | |
| 4,673,402 A | 6/1987 | Weisman et al. | |
| 4,673,403 A | 6/1987 | Lassen et al. | |
| 4,758,240 A | 7/1988 | Glassman | |
| 4,761,258 A * | 8/1988 | Enloe | 425/80.1 |
| 4,804,380 A | 2/1989 | Lassen et al. | |
| 4,848,572 A | 7/1989 | Herrera | |
| 4,886,632 A * | 12/1989 | Van Iten et al. | 425/290 |
| 4,904,249 A | 2/1990 | Miller et al. | |
| 4,935,022 A | 6/1990 | Lash et al. | |
| 4,988,344 A | 1/1991 | Reising et al. | |
| 5,127,911 A | 7/1992 | Baharav | |
| 5,248,309 A | 9/1993 | Serbiak et al. | |
| 5,308,346 A | 5/1994 | Sneller et al. | |
| 5,383,868 A | 1/1995 | Hyun | |
| 5,545,156 A | 8/1996 | Dipalma et al. | |
| 5,591,150 A | 1/1997 | Olsen et al. | |
| 5,599,337 A | 2/1997 | McCoy et al. | |
| 5,609,588 A | 3/1997 | Dipalma et al. | |
| 5,624,423 A | 4/1997 | Anjur et al. | |
| 5,628,739 A | 5/1997 | Hsieh et al. | |
| 5,649,916 A | 7/1997 | Dipalma et al. | |
| 5,702,380 A | 12/1997 | Walker | |
| 5,730,818 A | 3/1998 | Isakson | |
| 5,807,362 A | 9/1998 | Serbiak et al. | |
| 5,833,680 A | 11/1998 | Hartman | |
| 6,059,763 A | 5/2000 | Brown | |
| 6,100,442 A | 8/2000 | Samuelsson et al. | |
| 6,160,197 A | 12/2000 | Lassen et al. | |
| 6,175,056 B1 | 1/2001 | Carlucci et al. | |
| 6,191,340 B1 | 2/2001 | Carlucci et al. | |
| 6,217,691 B1 * | 4/2001 | Vair et al. | 156/176 |
| 6,293,931 B1 | 9/2001 | Romare | |
| 6,296,628 B1 | 10/2001 | Mizutani | |
| 6,306,123 B1 | 10/2001 | Salerno et al. | |
| 6,316,688 B1 | 11/2001 | Hammons et al. | |
| 6,350,257 B1 | 2/2002 | Björklund et al. | |
| 6,394,989 B2 | 5/2002 | Mizutani | |
| 6,410,822 B1 | 6/2002 | Mizutani | |
| 6,413,248 B1 | 7/2002 | Mizutani | |
| 6,417,427 B1 | 7/2002 | Roxendal et al. | |
| 6,441,268 B1 | 8/2002 | Edwardsson | |
| 6,482,193 B1 | 11/2002 | Samuelsson et al. | |
| 6,486,379 B1 | 11/2002 | Chen et al. | |
| 6,492,574 B1 | 12/2002 | Chen et al. | |
| 6,503,233 B1 | 1/2003 | Chen et al. | |
| 6,575,948 B1 | 6/2003 | Kashiwagi et al. | |
| 6,610,902 B1 | 8/2003 | Gustafsson et al. | |
| 6,617,490 B1 | 9/2003 | Chen et al. | |
| 6,632,206 B1 | 10/2003 | Onishi et al. | |
| 6,660,903 B1 | 12/2003 | Chen et al. | |
| 6,700,034 B1 | 3/2004 | Lindsay et al. | |
| 6,764,477 B1 | 7/2004 | Chen et al. | |
| 6,955,667 B1 | 10/2005 | Tanaka et al. | |
| 6,958,430 B1 | 10/2005 | Marinelli | |
| 7,001,167 B2 | 2/2006 | Venturino et al. | |
| 7,122,023 B1 | 10/2006 | Hinoki | |
| 7,323,072 B2 * | 1/2008 | Engelhart et al. | 156/73.2 |
| 7,368,627 B1 | 5/2008 | Widlund | |
| 7,438,708 B2 | 10/2008 | Kashiwagi et al. | |
| 7,597,690 B2 | 10/2009 | Tanio et al. | |
| 7,621,899 B2 | 11/2009 | Fujikawa et al. | |
| 2001/0021836 A1 | 9/2001 | Kashiwagi | |
| 2001/0029359 A1 | 10/2001 | Carlucci | |
| 2001/0044610 A1 | 11/2001 | Kim et al. | |
| 2002/0026170 A1 | 2/2002 | Samulesson et al. | |
| 2002/0052589 A1 | 5/2002 | Strand | |
| 2002/0055726 A1 | 5/2002 | Costa | |
| 2002/0065497 A1 | 5/2002 | Kolby | |
| 2002/0077617 A1 | 6/2002 | Drevik | |
| 2002/0082576 A1 | 6/2002 | Hansson et al. | |
| 2002/0087133 A1 | 7/2002 | Osterdahl et al. | |
| 2002/0087138 A1 | 7/2002 | Osterdahl et al. | |
| 2002/0156443 A1 | 10/2002 | Drevik et al. | |
| 2002/0156450 A1 | 10/2002 | Drevik et al. | |
| 2002/0165512 A1 | 11/2002 | Drevik et al. | |
| 2002/0165513 A1 | 11/2002 | Drevik et al. | |
| 2002/0188270 A1 | 12/2002 | Edens et al. | |
| 2002/0193758 A1 | 12/2002 | Sandberg | |
| 2003/0018314 A1 | 1/2003 | Nozaki et al. | |
| 2003/0040729 A1 | 2/2003 | Malowaniec et al. | |
| 2003/0055392 A1 | 3/2003 | Tagami et al. | |
| 2003/0088222 A1 | 5/2003 | Yoshimasa et al. | |
| 2003/0125699 A1 | 7/2003 | Drevik et al. | |
| 2003/0125700 A1 | 7/2003 | Drevik | |
| 2003/0125701 A1 | 7/2003 | Widlund | |
| 2003/0130643 A1 | 7/2003 | Drevik et al. | |
| 2003/0144644 A1 | 7/2003 | Murai et al. | |
| 2003/0167047 A1 | 9/2003 | Policappelli | |
| 2004/0254556 A1 | 12/2004 | Brisebois et al. | |
| 2005/0027278 A1 | 2/2005 | Mizutani et al. | |
| 2005/0080391 A1 | 4/2005 | Yoshimasa et al. | |
| 2006/0116653 A1 | 6/2006 | Munakata et al. | |
| 2006/0135930 A1 | 6/2006 | Mizutani et al. | |
| 2006/0142724 A1 | 6/2006 | Watanabe et al. | |
| 2006/0142725 A1 | 6/2006 | Fujikawa et al. | |
| 2006/0259002 A1 | 11/2006 | Parr | |
| 2006/0264878 A1 | 11/2006 | Carstens | |
| 2006/0271008 A1 | 11/2006 | Tanio et al. | |
| 2006/0287635 A1 | 12/2006 | Angel | |
| 2007/0005036 A1 | 1/2007 | Nishikawa et al. | |
| 2008/0065037 A1 | 3/2008 | Konawa | |
| 2008/0119810 A1 | 5/2008 | Kuroda et al. | |
| 2008/0172018 A1 | 7/2008 | Chien | |
| 2008/0275419 A1 | 11/2008 | Standfest | |
| 2008/0281287 A1 | 11/2008 | Marcelo et al. | |
| 2009/0036854 A1 | 2/2009 | Guidotti et al. | |
| 2009/0036858 A1 | 2/2009 | Van Den Bogart et al. | |
| 2009/0157032 A1 | 6/2009 | MacDonald et al. | |
| 2009/0281511 A1 | 11/2009 | Fukae | |
| 2009/0281515 A1 | 11/2009 | Noda et al. | |
| 2010/0030175 A1 | 2/2010 | Konawa | |
| 2010/0036355 A1 | 2/2010 | Håkansson et al. | |
| 2010/0057031 A1 | 3/2010 | Kuroda et al. | |
| 2010/0100067 A1 | 4/2010 | Pugliese, III | |

FOREIGN PATENT DOCUMENTS

| | | |
|---|---|---|
| EP | 668066 A2 | 8/1995 |
| EP | 680739 A1 | 11/1995 |
| EP | 733729 A1 | 3/1996 |
| EP | 768070 A1 | 4/1997 |
| EP | 774946 A1 | 5/1997 |
| EP | 472633 B2 | 11/1999 |
| EP | 335252 B1 | 12/2001 |
| EP | 1051956 B1 | 7/2004 |
| EP | 1493415 A3 | 5/2006 |
| EP | 2085504 A1 | 8/2009 |
| GB | 2202554 A | 3/1987 |
| JP | 2/121664 A | 5/1990 |
| JP | 4/146748 A | 5/1992 |
| JP | 8/299383 A | 11/1996 |
| JP | 10/137290 A | 5/1998 |
| JP | 10/328232 A | 12/1998 |
| JP | 11/033054 A | 2/1999 |
| JP | 11/042250 A | 2/1999 |
| JP | 11/226051 A | 8/1999 |
| JP | 11/299827 A | 11/1999 |
| JP | 2000/189456 A | 7/2000 |
| JP | 2001/224626 A | 8/2001 |
| JP | 2002/291795 A | 10/2002 |
| JP | 2003/062007 A | 3/2003 |
| JP | 2003/116909 A | 4/2003 |
| JP | 2003/135517 A | 5/2003 |
| JP | 2005/237793 A | 9/2005 |
| JP | 2005/296024 A | 10/2005 |
| JP | 2006/223854 A | 8/2006 |
| JP | 2006/239162 A | 9/2006 |
| JP | 2006/263205 A | 10/2006 |

| | | | |
|---|---|---|---|
| JP | 2006/297070 A | 11/2006 |
| JP | 2006/297076 A | 11/2006 |
| JP | 2007/037660 A | 2/2007 |
| JP | 2007/089818 A | 4/2007 |
| JP | 2007/089906 A | 4/2007 |
| JP | 2007/089907 A | 4/2007 |
| JP | 2007/097841 A | 4/2007 |
| JP | 2007/135943 A | 6/2007 |
| JP | 2007/181725 A | 7/2007 |
| JP | 2007/275491 A | 10/2007 |
| JP | 2008/080150 A | 4/2008 |
| JP | 2008/161256 A | 7/2008 |
| JP | 2008/161564 A | 7/2008 |
| JP | 2008/229032 A | 10/2008 |
| JP | 2008/229033 A | 10/2008 |
| JP | 2008/295475 A | 12/2008 |
| JP | 2009/112590 A | 5/2009 |
| JP | 2009/112864 A | 5/2009 |
| JP | 2009/195640 A | 9/2009 |
| JP | 2009/207598 A | 9/2009 |
| WO | WO 90/13278 A1 | 11/1990 |
| WO | WO 91/03999 A1 | 4/1991 |
| WO | WO 96/07379 A1 | 3/1996 |
| WO | WO 97/04730 A2 | 2/1997 |
| WO | WO 97/05840 A1 | 2/1997 |
| WO | WO 97/09014 A1 | 3/1997 |
| WO | WO 97/09017 A1 | 3/1997 |
| WO | WO 97/14390 A1 | 4/1997 |
| WO | WO 97/33543 A1 | 9/1997 |
| WO | WO 97/40798 A1 | 11/1997 |
| WO | WO 98/00083 A1 | 1/1998 |
| WO | WO 98/14152 A1 | 4/1998 |
| WO | WO 98/22058 A1 | 5/1998 |
| WO | WO 98/22060 A1 | 5/1998 |
| WO | WO 98/58614 A1 | 12/1998 |
| WO | WO 99/55269 A1 | 11/1999 |
| WO | WO 00/00121 A1 | 1/2000 |
| WO | WO 00/02509 A1 | 1/2000 |
| WO | WO 01/17474 A1 | 3/2001 |
| WO | WO 01/35887 A1 | 5/2001 |
| WO | WO 01/67982 A2 | 9/2001 |
| WO | WO 01/97736 A1 | 12/2001 |
| WO | WO 02/41817 A1 | 5/2002 |
| WO | WO 02/45637 A1 | 6/2002 |
| WO | WO 02/47594 A1 | 6/2002 |
| WO | WO 02/085269 A1 | 10/2002 |
| WO | WO 02/085270 A1 | 10/2002 |
| WO | WO 02/087483 A1 | 11/2002 |
| WO | WO 02/087484 A1 | 11/2002 |
| WO | WO 03/047483 A1 | 6/2003 |
| WO | WO 03/047484 A1 | 6/2003 |
| WO | WO 03/053301 A1 | 7/2003 |
| WO | WO 03/055431 A1 | 7/2003 |
| WO | WO 03/059222 A1 | 7/2003 |
| WO | WO 03/099182 A1 | 12/2003 |
| WO | WO 2005/048899 A1 | 6/2005 |
| WO | WO 2006/084304 A1 | 8/2006 |
| WO | WO 2006/130646 A1 | 12/2006 |
| WO | WO 2009/074896 A1 | 6/2009 |
| WO | WO 2009/115931 A2 | 9/2009 |
| WO | WO 2010/017360 A1 | 2/2010 |

* cited by examiner

APPARATUS FOR MAKING A FIBROUS ARTICLE HAVING A THREE DIMENSIONAL PROFILE

FIELD OF THE INVENTION

The present invention generally relates to a method and apparatus for a making a formed fibrous article and more specifically to method and apparatus for making a formed fibrous article useful as an absorbent core structure in a disposable sanitary article such as a sanitary napkin, panty liner, diaper or the like. The present invention also relates to a disposable sanitary article including a formed fibrous article according to the present invention as a core structure thereof.

BACKGROUND OF THE INVENTION

Various methods for making formed fibrous articles from fibrous materials such as cellulose or the like are well know to those of skill in the art. One common method of manufacturing such formed fibrous articles consists of defiberizing a starting material and then creating an air-entrained stream of the defiberized material. The air-entrained defiberized material may be formed into a formed fibrous article through the use of a porous mold structure subjected to a vacuum to draw the defiberized material into the mold.

It is also known that formed fibrous articles of the type described above may be subjected to calendering processes to alter the mechanical and fluid handling properties of such articles. A calendering process used in the art is commonly referred to as "pin calendering". Pin calendering employs the use of a plurality of pins adapted to compress and densify the article.

A problem associated with pin calendering processes of the type described above is that such processes typically require that a "carrier layer" be used during the pin-calendering step. "Carrier layer" as used herein means any material layer used to support the formed fibrous article, such as a conveyer belt or an adjacent material layer such as rolled nonwoven layer or the like. The use of a carrier layer increases complexity of manufacture. In addition, if the carrier layer is a layer intended to be incorporated into the final product, the inclusion of such layer may increase the cost of the final product and/or undesirably affect the fluid handling characteristics of the product.

In view of the above the inventors of the present invention have discovered, and disclosed herein, a method and apparatus for making a pin-calendered formed fibrous article that does not require the use of a carrier layer. Formed fibrous articles according to the present invention are particularly useful as an absorbent core structure in a disposable sanitary article such as a sanitary napkin, panty liner, diaper or the like.

SUMMARY OF THE INVENTION

In view of the foregoing, the present invention provides an apparatus for making a formed fibrous article having a three dimensional profile, the apparatus including a calendering station including a first roll and a second roll, wherein the second roll includes at least one recess for providing a formed fibrous article with a three dimensional profile, a pin calendering station including a first roll and a second roll, wherein the first roll and second roll are structured and arranged to convey a fibrous article through a nip defined between the first and second roll without the use of a carrier layer.

BRIEF DESCRIPTION OF THE DRAWINGS

Examples of embodiments of the present invention will now be described with reference to the drawings, in which.

DETAILED DESCRIPTION OF THE INVENTION

Referring to FIGS. 1-9 and 11-20, there is illustrated a preferred apparatus 10 for making a formed fibrous article 12 according to the method of the present invention.

Figure 1:
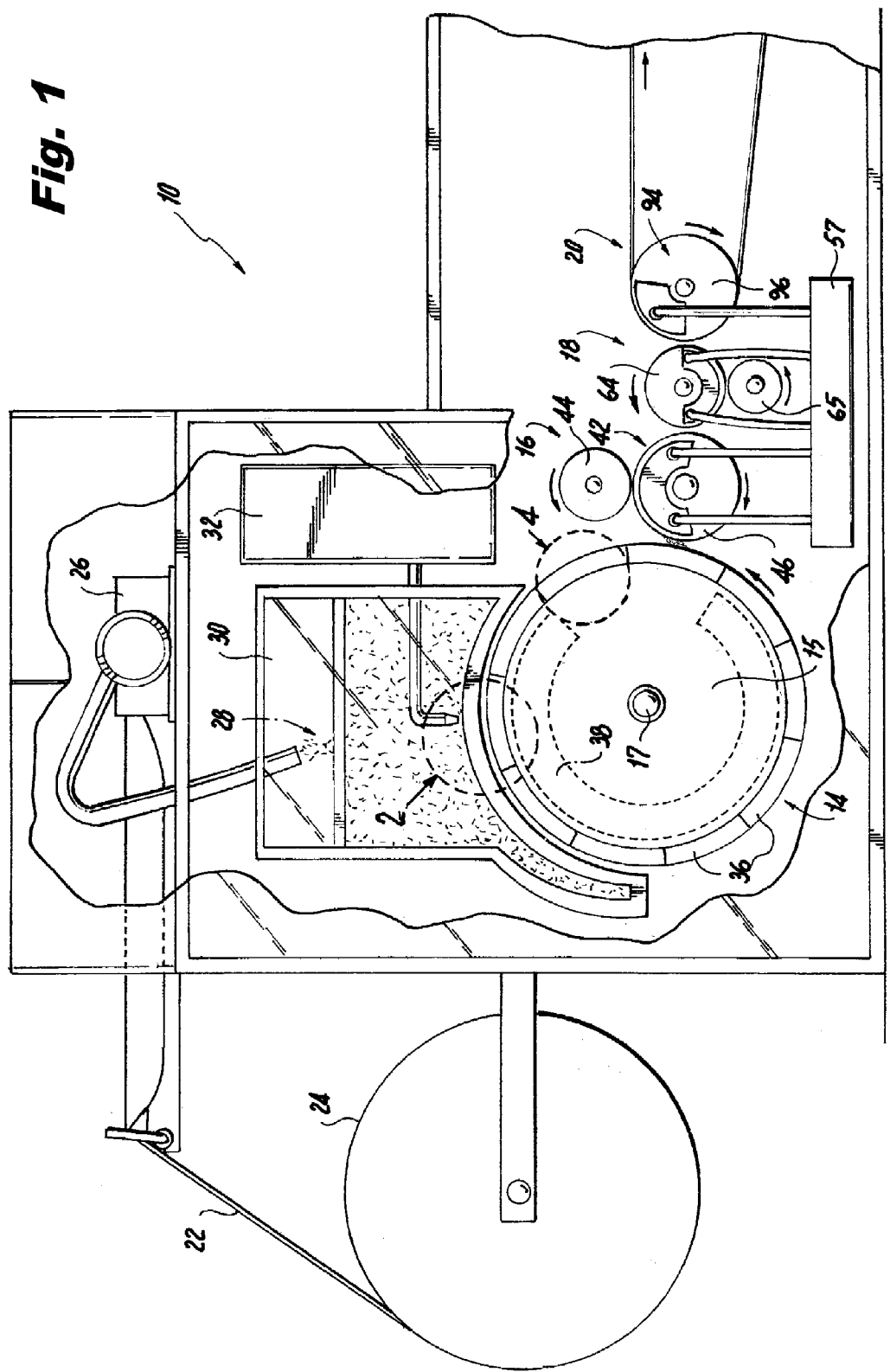
FIG. 1 is a side elevation view of an apparatus according to the present invention.
Figure 2:
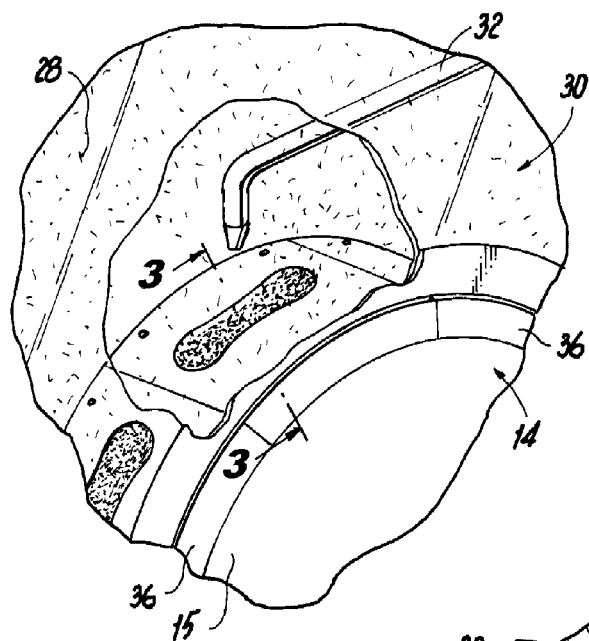
FIG. 2 is a detailed perspective view of the forming drum that forms part of the apparatus according to the present invention.

As shown in FIG. 1, the apparatus 10 according to the present invention generally includes a forming drum 14, a calendering station 16, a pin calendering station 18, and a transfer wheel 20. Certain details of the apparatus 10, such as electrical lines, have been omitted from the figures to simplify the same. However, these features and other basic elements of the apparatus will be clear to those of skill in the art.

The formed fibrous article 12, which is depicted during various stages of the method according to the present invention in FIGS. 3, 5-6, 8, 10, 12 and 18-22, preferably is formed from cellulosic fibers, and in a preferred embodiment of the invention, includes a mixture of cellulosic fibers and superabsorbent polymer. Cellulosic fibers that can be used in the formed fibrous article 12 are well known in the art and include wood pulp, cotton, flax and peat moss. Wood pulp is preferred. Both softwood and hardwood species are useful. Softwood pulps are preferred.

The fibrous article 12 may also contain any superabsorbent polymer (SAP), which are well known in the art. For the purposes of the present invention, the term "superabsorbent polymer" (or "SAP") refers to materials, which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. of Osaka, Japan, under the designation of SA70N and products offered by Stockhausen Inc.

The pulp used to form the fibrous article 12 is preferably a bleached softwood pulp, produced by a Kraft process. As shown in FIG. 1, the pulp is provided by the manufacturer as a pulp board 22 in rolled form, the roll identified by the reference numeral 24. The pulp board 22 is conveyed from the roll 24 to a device 26 for grinding the pulp board 22 into fibrous pulp 28. The fibrous pulp 28 is released from the grinding device 26 into a chamber 30 for holding the fibrous pulp 28. The apparatus 10 may further optionally include a device 32 for introducing superabsorbent polymer into the chamber 30 to thereby form a fibrous pulp and superabsorbent mixture. Any conventional device suitable for this purpose, and known to those of skill in the art, may be used for introducing the superabsorbent into the chamber 30.

Figure 3:
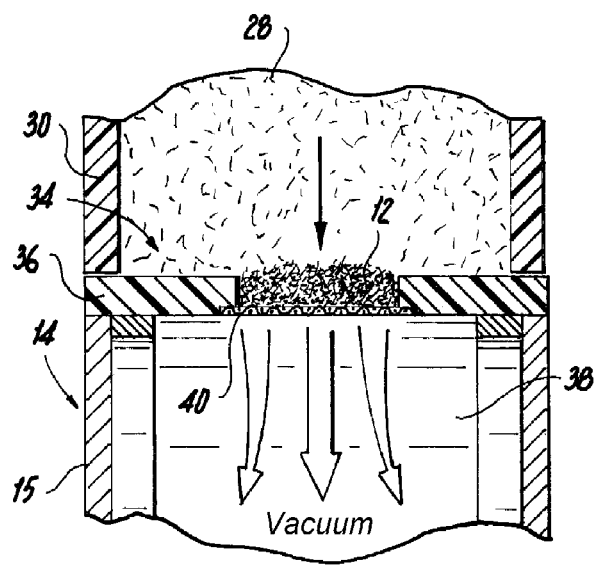
FIG. 3 is a sectional view taken along line 3-3 in FIG. 2.

As best seen in FIG. 3, the chamber 30 has a partially open bottom portion 34 that communicates with the forming drum 14. As seen in FIG. 1, the forming drum 14 includes a hollow cylinder 15 that is structured and arranged to rotate about a fixed axis 17. Any conventional means to rotate the cylinder 15, well known to those of skill in the art, may be used to rotate the cylinder 15. As shown in FIGS. 1-4, the cylinder 15 has a plurality of molds 36 mounted thereto. As the cylinder 15 rotates, each of the molds 36 are sequentially arranged in communication with the open portion 34 of the chamber 30 to thereby receive fibrous pulp 28 from the chamber 30. In FIG. 1, the cylinder 15 rotates in a counterclockwise manner during operation of the apparatus 10.

Figure 4:
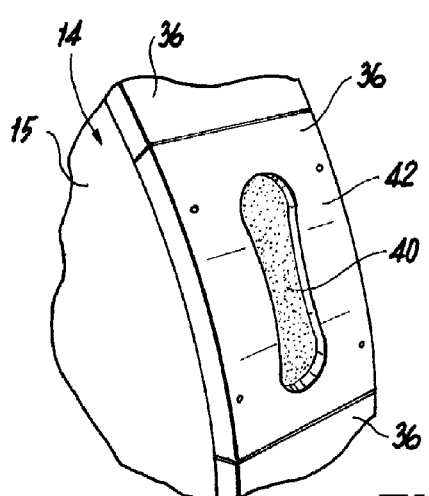
FIG. 4 is a detailed perspective view of a portion of the forming drum shown in FIG. 2.

As shown in FIGS. 1 and 3, the forming drum 14 further includes a vacuum chamber 38 arranged within the interior of the cylinder 15. The vacuum chamber 38 is arranged in a fixed location relative to the rotating cylinder 15 and is operably coupled to a vacuum source (not shown). As best seen in FIG. 4, the mold 36 includes a porous screen 40 structure in the shape of the formed fibrous article 12 to be formed in the mold 36. As the mold 36 passes over the vacuum chamber 38 of the forming drum 14 the vacuum functions to draw the fibrous pulp 28 from the chamber 30 into the mold 36 by drawing air through the porous screen 40 of the mold 36.

As shown in detail in FIG. 4, the mold 36 includes a nonporous mounting plate portion 42 that surrounds the porous screen 40 portion of the mold 36. The mounting plate portion 42 of the mold 36 is mounted to the periphery 44 of the cylinder 15, thereby enabling each of the molds 36 to rotate with the rotating cylinder 15.

After the mold 36 is rotated under the partially open bottom portion 34 of the chamber 30, the mold 36 is further rotated by the rotating cylinder 15, and as described in further detail below, the fibrous article 12 is then transferred to the calendering station 16.

After formation in the mold 36, the formed fibrous article 12 preferably has a basis weight in the range of between about 200 gsm (g/m$^2$) to about 400 gsm, a thickness in the range of about 5 mm to about 20 mm, and a density in the range of about 0.01 g/cc to about 0.03 g/cc.

Figure 5:
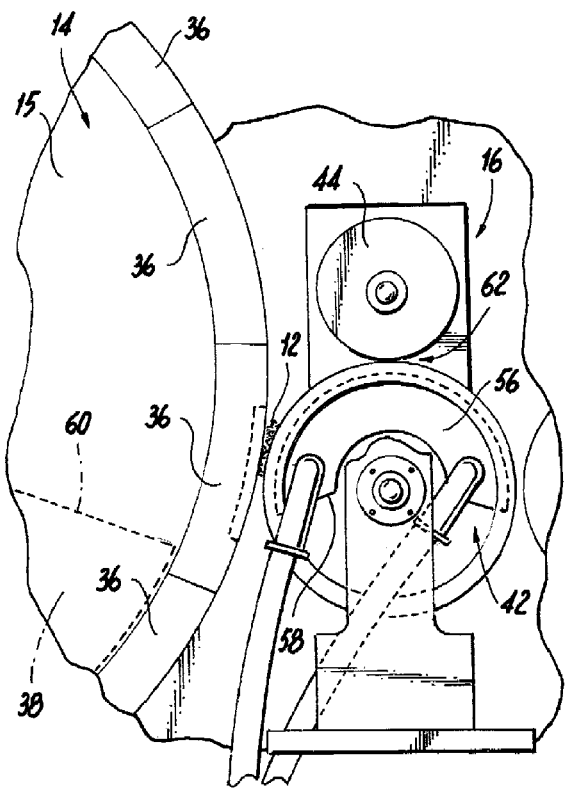
FIG. 5 is a side elevation view of the forming drum and a calendering station that form part of the apparatus according to the present invention.
Figure 6:
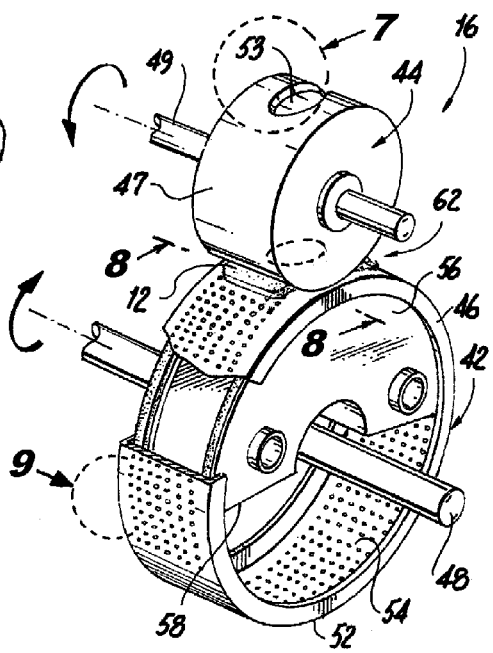
FIG. 6 is a detailed perspective view of the calendering station shown in FIG. 5, depicting the vacuum roll and calender roll thereof.
Figure 7:
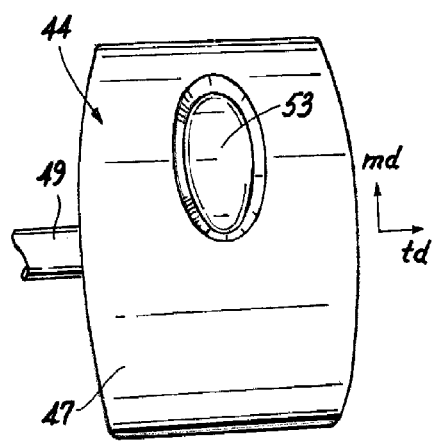
FIG. 7 is a elevation view of the that portion of the calendering station calender roll circled in FIG. 6.
Figure 8:
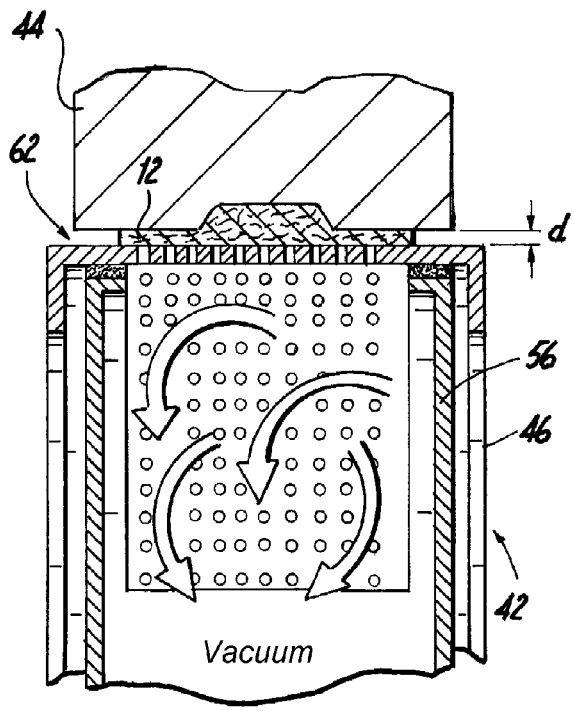
FIG. 8 is a sectional view taken along line 8-8 in FIG. 6.
Figure 9:
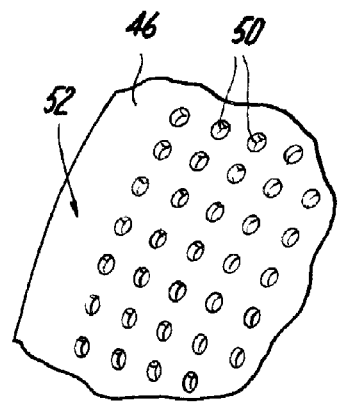
FIG. 9 is a detailed perspective view of that portion of the calendering station vacuum roll circled in FIG. 6.

As shown in FIGS. 1 and 5-9 the calendering station 16 generally includes a vacuum roll 42 and an opposed calender roll 44. As best seen in FIG. 6, the vacuum roll 42 is formed from a rotatable cylinder 46 that is rotatable about a fixed axis 48. The calender roll 44 is rotatable about a fixed axis 49. Any conventional means to rotate the cylinder 46, and calender roll 44, well known to those of skill in the art, may be used to rotate cylinder 46 and calender roll 44. The cylinder 46 rotates in a clockwise manner during operation of the apparatus 10, and the calender roll 44 rotates in a counterclockwise manner, as show in FIG. 1. As best seen in FIGS. 6, 8 and 9, the cylinder 46 includes a plurality of holes 50 that extend from the outer surface 52 of the cylinder 46 to the inner surface 54 of the cylinder 46.

As shown in detail in FIG. 7, the surface 47 of the calender roll 44 includes a recess 53. The recess 53 may take any number of different shapes including generally oval, elliptical, circular or the like. In one preferred embodiment of the invention, as shown in FIG. 7, the recess generally has an oval shape. Preferably, the recess 53 extends over a surface area in range of about 500 mm$^2$ to about 5000 mm$^2$. The recess 53 preferably has a depth in the range of about 2 mm to about 25 mm as measured from the surface 47 of the roll 44 located outside the recess 53. The recess 53 is preferably arranged such that it is longer in the machine direction (md) than in the transverse direction (td). Preferably, the recess 53 has a maximum length, as measured in the machine direction, in the range of about 20 mm to about 120 mm and a maximum width, as measured in the transverse direction, in the range of about 5 mm to about 60 mm.

As shown in FIGS. 5, 6 and 8, the vacuum roll 42 further includes a vacuum chamber 56 arranged within the interior of the cylinder 46. The vacuum chamber 56 is arranged in a fixed location relative to the rotating cylinder 46 and is operably coupled to a vacuum source 57 (FIG. 1). The vacuum chamber 56 is arranged in flow communication with the plurality of holes 50 that extend through the cylinder 46 and thereby draws air through said holes 50.

As shown in FIG. 5, the vacuum chamber 56 is arranged such that its leading edge 58 is substantially aligned with a trailing edge 60 of the vacuum chamber 38 located within cylinder 15 of the forming drum 14. This arrangement of the vacuum chamber 56 relative to location of the vacuum chamber 38 effectuates a transfer of the formed fibrous article 12 from within the mold 36 on the forming drum 14 to the vacuum roll 42.

Once the formed fibrous article 12 has been transferred to the cylinder 46 of the vacuum roll 42 the cylinder 46 rotates the fibrous 12 article until the article 12 passes through the nip 62 formed between the vacuum roll 42 and the calender roll 44. The nip 62 preferably uniformly compresses the fibrous article 12 outside of the area defined by recess 53. The compression of the fibrous article 12 results in a reduction in thickness of the article 12 and a corresponding increase in density in that portion of the fibrous article 12 located outside of the area of the recess 53. In a preferred embodiment of the invention the nip 62 has a distance "d" (i.e. the distance between the surfaces of the opposed rolls) of about 0.9 mm. The distance "d" is identified by the reference symbol "d" in FIG. 8.

Figure 10:
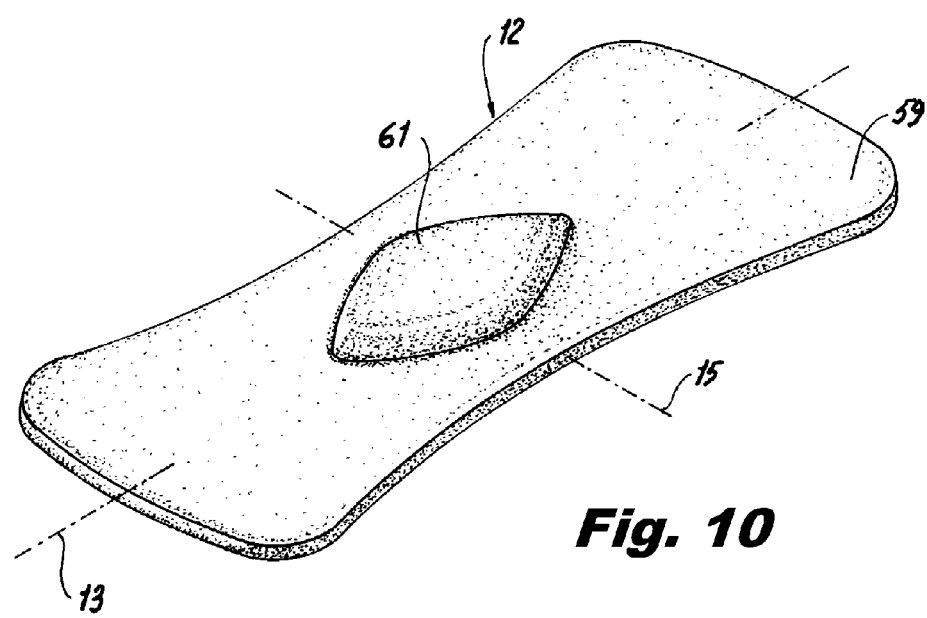
FIG. 10 is a perspective view of a formed fibrous article according to the invention after passing through the calendering station.

As shown in FIG. 10, after passing through the nip 62 the fibrous article 12 generally includes two areas 59 and 61. The first area 59, corresponds to that portion of the article 12 that has been compressed by the rolls 42 and 44 outside of the area of the recess 53. Area 59 preferably extends over a surface area of between about 7000 $mm^2$ and 14000 $mm^2$, has a thickness in the range of about 4 mm to about 12 mm, and a density in the range of about 0.02 g/cc to about 0.1 g/cc. Area 61 of the article 12 is that portion of the article 12 corresponding in location to the recess 53. Area 61 preferably extends over a surface area of between about 1000 $mm^2$ and 7000 $mm^2$, has a thickness in the range of about 10 mm to about 20 mm, and a density in the range of about 0.01 g/cc to about 0.04 g/cc.

It is noted that the fibrous article 12, after passing through the nip 62, has a three dimensional profile. Specifically, area 59 of the fibrous article defines a substantially planar portion of the fibrous article 12 and area 61 extends upwardly from the substantially planar portion thereby defining an upwardly extending hump or raised portion. In one preferred embodiment of the invention, as shown in FIG. 10, area 61 is symmetrically arranged with respect to longitudinally extending central axis 13 of the fibrous article and the transversely extending central axis 19 of the fibrous article 12

It is noted that the fibrous article 12 has a three dimensional profile yet has a constant basis weight throughout its entire structure. Specifically, planar portion 59 and the raised portion 61 are both formed from a common material composition having a constant basis weight, yet differ in thickness and density. It is also noted that the entire fibrous article 12 is formed from a single material layer.

After the article 12 passes through the nip 62 the article 12 is further rotated in a clockwise direction by the cylinder 46 of the vacuum roll 43, and as will be described in further detail below, transferred to the pin calendering station 18.

Figure 11:
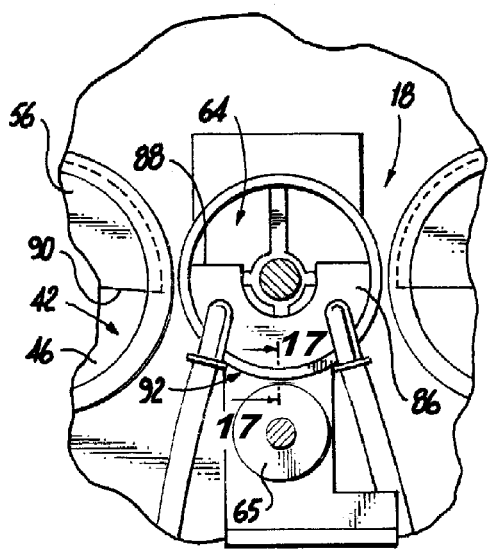
FIG. 11 is a side elevation view of a pin calendering station that forms part of the apparatus according to the present invention.
Figure 12:
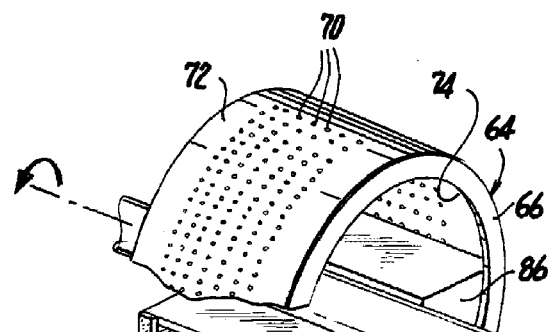
FIG. 12 is a detailed perspective view of the pin calendering station shown in FIG. 11, depicting the vacuum roll and pin calender roll thereof.

As shown in FIGS. 1 and 11-18 the pin calendering station 18 generally includes a vacuum roll 64 and an opposed pin calender roll 65. As best seen in FIG. 12, the vacuum roll 64 is formed from a rotatable cylinder 66 that is rotatable about a fixed axis 68. Any conventional means to rotate the cylinder 66, well known to those of skill in the art, may be used to rotate the cylinder 66. The cylinder 66 rotates in a counter-clockwise direction during operation of the apparatus 10. As shown in FIG. 12, the cylinder 66 includes a plurality of holes 70 that extend from the outer surface 72 of the cylinder 66 to the inner surface 74 of the cylinder 66. In a preferred embodiment of the invention each of the plurality of holes 70 has a diameter of about 1.5 mm and is spaced from an adjacent hole by a distance of about 4 mm (center to center).

Figure 13:
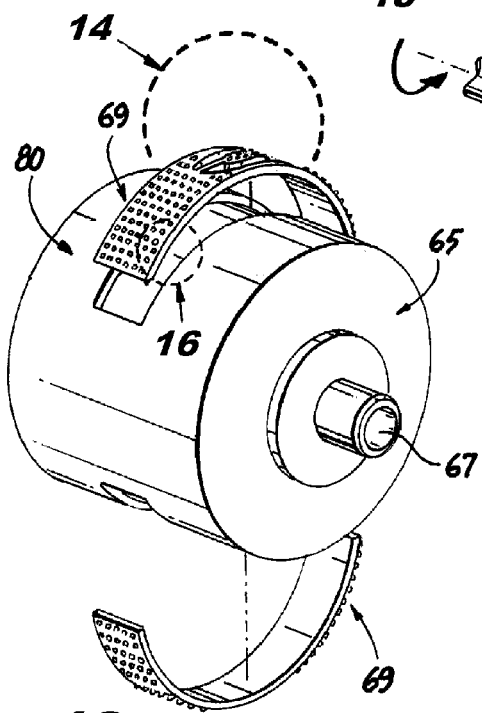
FIG. 13 is a partially exploded perspective view of the pin calendering station pin calender roll.
Figure 14:
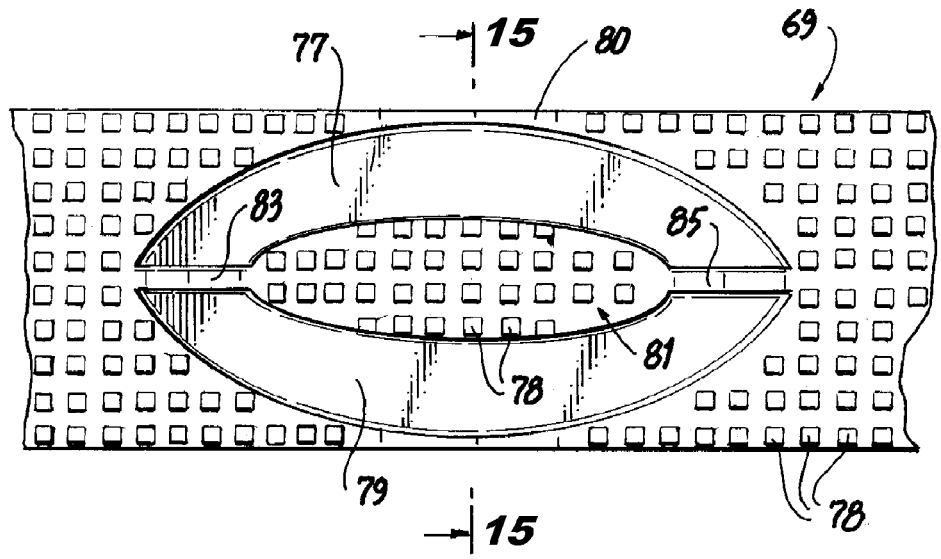
FIG. 14 is a detailed plan view of that portion of the pin calender roll circled in FIG. 13.
Figure 15:
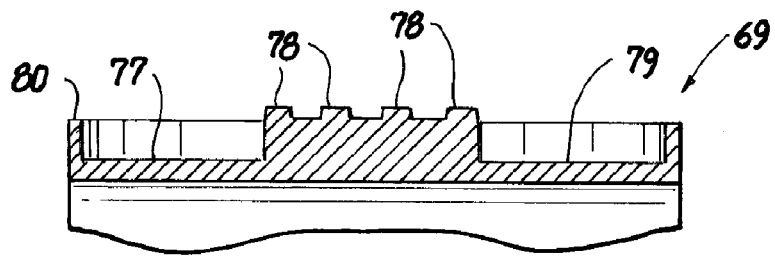
FIG. 15 is a sectional view taken along line 15-15 in FIG. 14.
Figure 16:
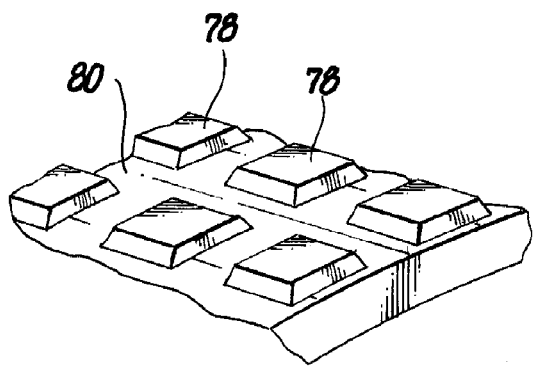
FIG. 16 is detailed perspective view of that portion of the pin calender roll circled in FIG. 13.

As shown in FIGS. 12 and 13 the pin calender roll 65 is structured and arranged to rotate about a fixed axis 67. Any conventional means to rotate the pin calender roll, well known to those of skill in the art, may be used to rotate the roll 65. As shown in FIGS. 13 and 14 the pin calender roll 65 has a roll surface 80 including a first area 69 having plurality of individual pins 78 that extend outwardly from a surface 80 of the roll 65. As shown in FIG. 13, the first area 69 extends down a central portion of the roll surface 80. In a preferred embodiment of the invention, the first area 69 is structured and arranged to emboss a central region of the fibrous article 12. Alternatively, the first area 69 may be arranged to emboss substantially the entire fibrous article 12.

As best seen in FIG. 14, the surface 80 of the roll 65 is further provided with a first recess 77 and a second recess 79. Each of the first recess 77 and second recess 79 are structured and arranged to correspond in location to area 61 of the fibrous article 12 when the article 12 passes through the nip 92 defined between the vacuum roll 64 and the pin calender roll 65. Preferably each recess 77 and 79 extends over a surface area of between about 260 $mm^2$ and 1100 $mm^2$ and has a depth of between about 2 mm and 25 mm.

As shown in FIG. 14, in a preferred embodiment of the invention, each recess 77 and 79 is generally arcuate in shape and generally extends in a machine direction. Each recess 77 and 79 is preferably positioned on the roll 65 so that it is symmetrically arranged with respect to the other recess about the longitudinally extending central axis 13 of the fibrous article and the transversely extending central axis 19 of the fibrous article 12, as the article 12 passes through the through the nip 92 defined between the vacuum roll 64 and the pin calender roll 65.

Recess 77 is separated from recess 79 by a land area 81 that includes a plurality of pins 78. Preferably the land area 81 has a surface area of between about 250 $mm^2$ and 1000 $mm^2$. The land area 81 is connected to the first area 67 by a first smooth roll surface segment 83 and second smooth roll surface segment 85, each of the segments 83 and 85 being preferably free of pins 78.

In preferred embodiments of the invention each of the pins 78 are spaced from an adjacent pin by a distance of about 4 mm (center to center), have height of about 1.5 mm and have an effective contact area of from about 0.8 $mm^2$ to about 1.2 $mm^2$.

Figure 17:
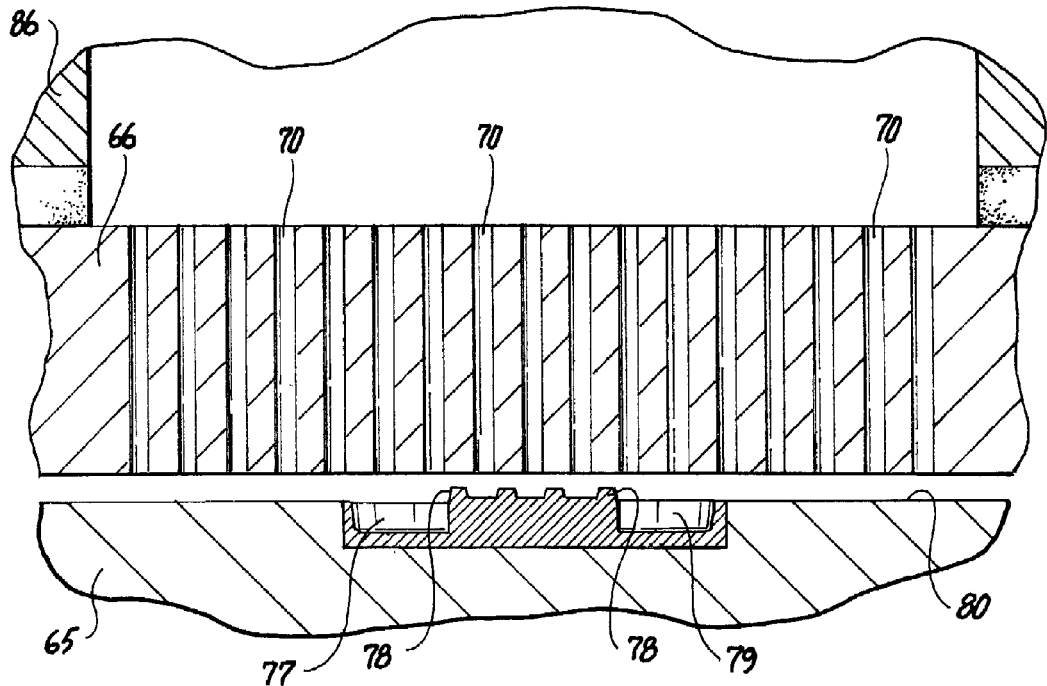
FIG. 17 is a sectional view taken along line 17-17 in FIG. 11.
Figure 18:
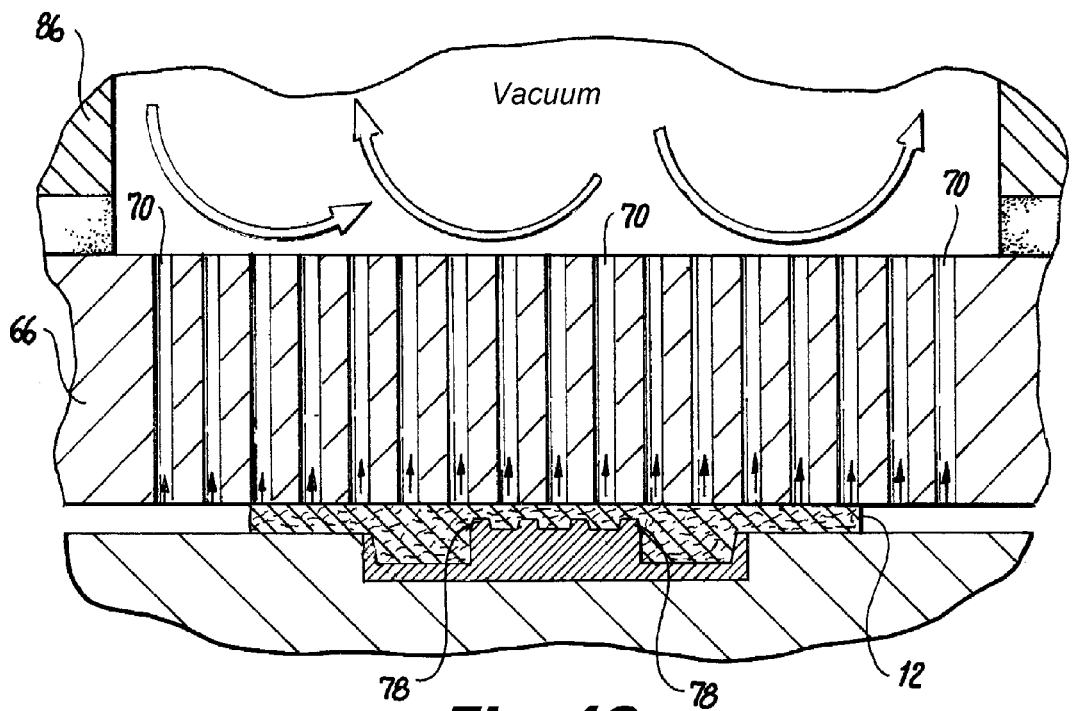
FIG. 18 is a sectional view taken along line 18-18 in FIG. 12.

As shown in FIGS. 17 and 18, each of the pins 78 are arranged such that they do not overlap with any of the plurality of holes 70 in the cylinder 66 of the vacuum roll 64. This arrangement of the pins 78 relative to the holes 70 insures that no pulp is forced into any of the plurality of holes 70, thereby improving the efficiency of pulp use and the efficiency of the process as a whole.

As shown in FIGS. 11-12 and 17-18, the vacuum roll 64 further includes a vacuum chamber 86 arranged within the interior of the cylinder 66. The vacuum chamber 86 is arranged in a fixed location relative to the rotating cylinder 66 and is operably coupled to the vacuum source 57 (FIG. 1). The vacuum chamber 86 is arranged in flow communication with the plurality of holes 70 that extend through the cylinder 66 and thereby draws air through said holes 70.

As shown in FIG. 11, the vacuum chamber 86 is arranged such that its leading edge 88 is substantially aligned with a trailing edge 90 of the vacuum chamber 56 located within the cylinder 46 of the vacuum roll 42. This arrangement of the vacuum chamber 86 relative to the location of the vacuum chamber 56 effectuates a transfer of the formed fibrous article 12 from the vacuum roll 42 to the vacuum roll 64.

Once the formed fibrous article 12 has been transferred to the cylinder 66 of the vacuum roll 64, the cylinder 66 rotates the formed fibrous article 12 until the article 12 passes through the nip 92 formed by the vacuum roll 64 and the pin calender roll 65.

In a preferred embodiment of the invention the nip 92 has a distance (i.e. the distance between the surfaces of the opposed rolls) of about 0.8 mm. Also in a preferred embodiment of the invention the pin calender roll 65 is heated to a temperature of between about 176° F. to about 212° F. by means of any suitable conventional heating means. It has been found that heating the pin calender roll 65 in this manner helps prevent the formed fibrous article 12 from adhering to the surface of the pin calender roll 65.

After the article 12 passes through the nip 92 the article 12 is further rotated in a counter clockwise direction by the cylinder 66 of the vacuum roll 64 as shown and, as will be described in further detail below, transferred to the transfer wheel 20.

Figure 19:
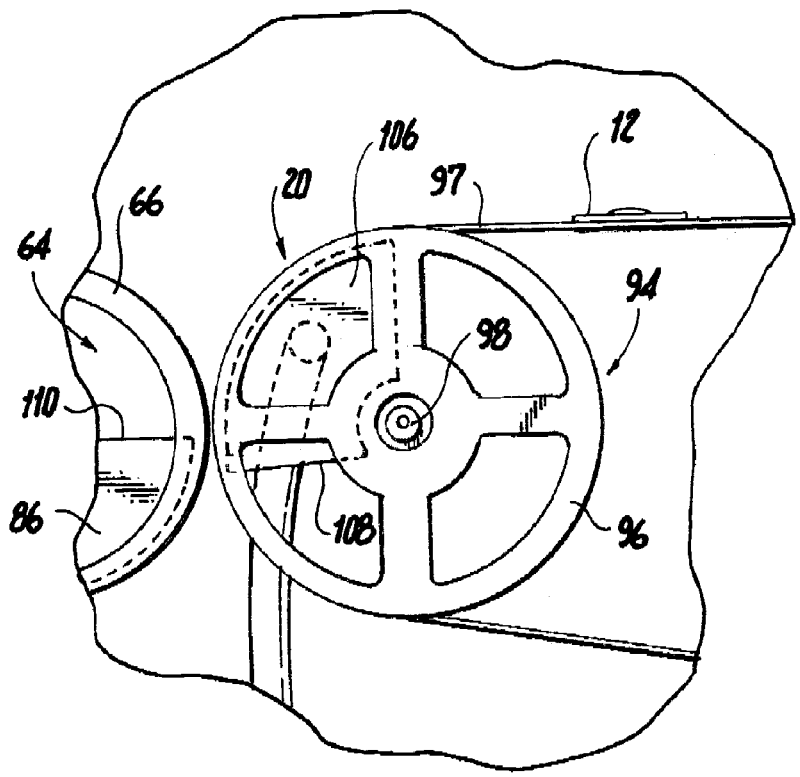
FIG. 19 is a side elevation view of a transfer wheel that forms part of the apparatus according to the present invention.
Figure 20:
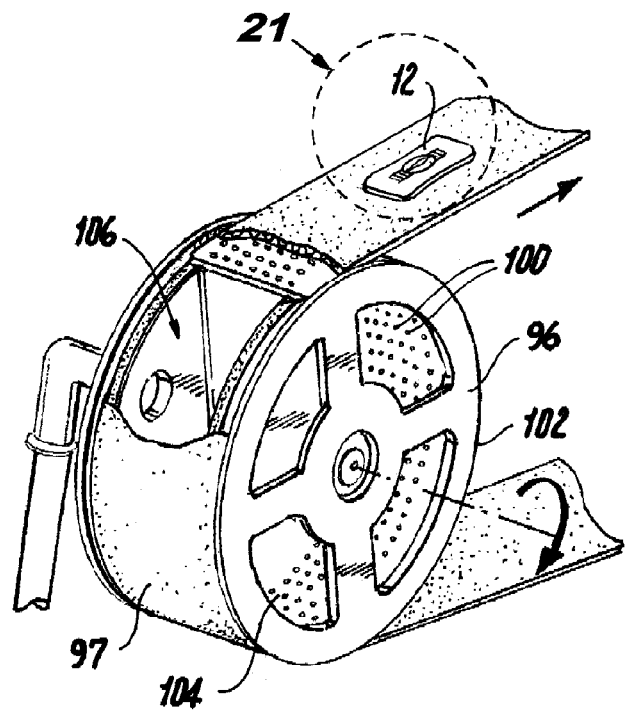
FIG. 20 is a perspective view of the transfer wheel shown in FIG. 19.

As shown in FIG. 19 the transfer wheel 20 comprises a vacuum roll 94 that is formed from a rotatable cylinder 96 that is rotatable about a fixed axis 98. Any conventional means to rotate the cylinder 96, well known to those of skill in the art, may be used to rotate the cylinder 96. The cylinder 96 rotates in a counterclockwise manner during operation of the apparatus 10, as show in FIG. 1. As shown in FIG. 20, the cylinder 96 includes a plurality of holes 100 that extend from the outer surface 102 of the cylinder 96 to the inner surface 104 of the cylinder 96.

As shown in FIGS. 19 and 20, the vacuum roll 94 further includes a vacuum chamber 106 arranged within the interior of the cylinder 96. The vacuum chamber 106 is arranged in a fixed location relative to the rotating cylinder 96 and is operably coupled to the vacuum source 57 (FIG. 1). The vacuum chamber 106 is arranged in flow communication with the plurality of holes 100 that extend through the cylinder 96 and thereby draw air through said holes 100.

The transfer wheel 20 further includes a porous conveyor belt 97 that extends around the cylinder 96 and travels with the cylinder 96, i.e. in a clockwise direction shown in FIG. 20.

As shown in FIG. 19, the vacuum chamber 106 is arranged such that its leading edge 108 is substantially aligned with a trailing edge 110 of the vacuum chamber 86 located within the cylinder 66 of the vacuum roll 64. This arrangement of the vacuum chamber 106 relative to the location of the vacuum chamber 86 effectuates a transfer of the formed fibrous article 12 from the vacuum roll 64 to the vacuum roll 94. Specifically, formed fibrous article 12 is transferred to the conveyor belt 97 and held in place by the vacuum chamber 106 that functions to draw air through the porous conveyor belt 97 via the holes 100 in the cylinder 96.

Once the fibrous article 12 is rotated past vacuum chamber 106, the porous conveyer belt 97 functions to further convey the formed fibrous article 12 in a machine direction. The formed fibrous article 12 may be conveyed in a machine direction for incorporation into a final product structure such as a sanitary napkin, panty liner, incontinence article, diaper or the like.

Figure 21:
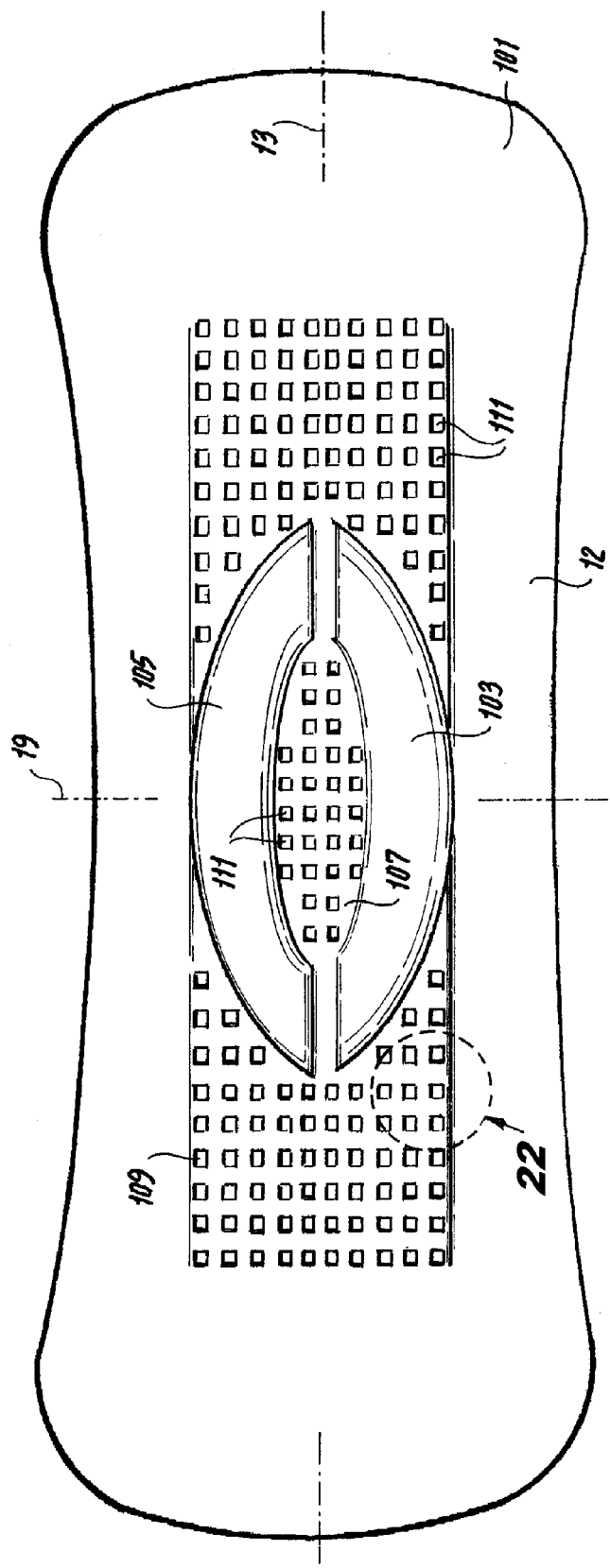
FIG. 21 is a top plan view of the formed fibrous article after passing through the pin calendering station.
Figure 22:
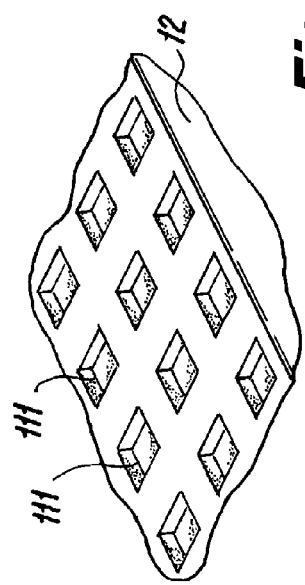
FIG. 22 is a detailed perspective view of that portion of the formed fibrous article circled in FIG. 21.

Referring to FIGS. 21 and 22, the completed fibrous article 12 generally includes an area 101 that has not been pin embossed, a first arcuate raised area 103, a second arcuate raised area 105, a pin embossed region 107 located between the raised area 103 and raised area 105, and a centrally extending pin embossed area 109 extending along the longitudinally extending central axis 13 of the article 12. Each of the pin embossed regions 107 and 109 include a plurality of depressions 111 corresponding in location to the pins 78. Areas 101 and 109 cooperate to define a substantially planar portion of the fibrous article 12 and raised areas 103 and 105 extend upwardly relative to the planar portion of the fibrous article 12.

After passing through the nip 92 area 101 preferably has a thickness in the range of about 0.8 mm to about 3.5 mm, a density in the range of about 0.06 g/cc to about 0.5 g/cc, and extends over a surface area of from about 6400 mm$^2$ and 9400 mm$^2$.

After passing through the nip 92 each of area 103 and 105 preferably has a thickness in the range of about 2 mm to about 10 mm and a density in the range of about 0.01 g/cc to about 0.1 g/cc. Each area 103 and 105 preferably extends over a surface area of from about 260 mm$^2$ and 1100 mm$^2$.

After passing through the nip 92 area 107 preferably has a thickness in the range of about 0.2 mm to about 1 mm, a density in the range of about 0.1 g/cc to about 0.9 g/cc in those areas 111 embossed by the pins 78 and a thickness in the range of about 0.8 mm to about 3.5 mm and a density in the range of about 0.06 g/cc to about 0.5 g/cc in those areas outside of areas 111. Area 107 preferably extends over a surface area of from about 250 mm$^2$ and 1000 mm$^2$.

After passing through the nip 92 area 109 preferably has a thickness in the range of about 0.2 mm to about 1.0 mm and a density in the range of about 0.1 g/cc to about 0.9 g/cc in those areas 111 embossed by the pins 78 and a thickness in the range of about 0.8 mm to about 3.5 mm and a density in the range of about 0.06 g/cc to about 0.5 g/cc in those areas outside of areas 111. Area 109 preferably extends over a surface area of from about 2400 mm$^2$ and 7600 mm$^2$.

It is noted that although the different areas of the fibrous article 12 differ in density and thickness the fibrous article 12 has a uniform basis weight throughout its entire structure. It is further noted that although fibrous article 12 according to the present invention possesses at least one raised area, i.e. the article 12 possesses a three dimensional profile, the article 12 has a uniform basis weight. Preferred embodiments of the present invention also present the above characteristics while being formed from a uniform material composition. In addition, in preferred embodiments of the present invention, the fibrous article 12 is formed from a single material layer.

It is noted that the formed fibrous article 12 is formed and pin-calendered without the use of any "carrier layer". In addition, is noted that the fibrous article is transferred from the forming drum 14 to the calendering station 16 then to the pin calendering station 18 without the use of any "carrier layer". "Carrier layer" as used herein means any material layer used to support the fibrous article, such as a conveyer belt or an adjacent material layer such a rolled nonwoven layer or the like.

In connection with the various vacuum chambers disclosed herein any suitable vacuum source may be employed. In a preferred embodiment of the invention the vacuum source is an air blower having an air flow of about 2,200 cubic meters per hour.

Figure 23:
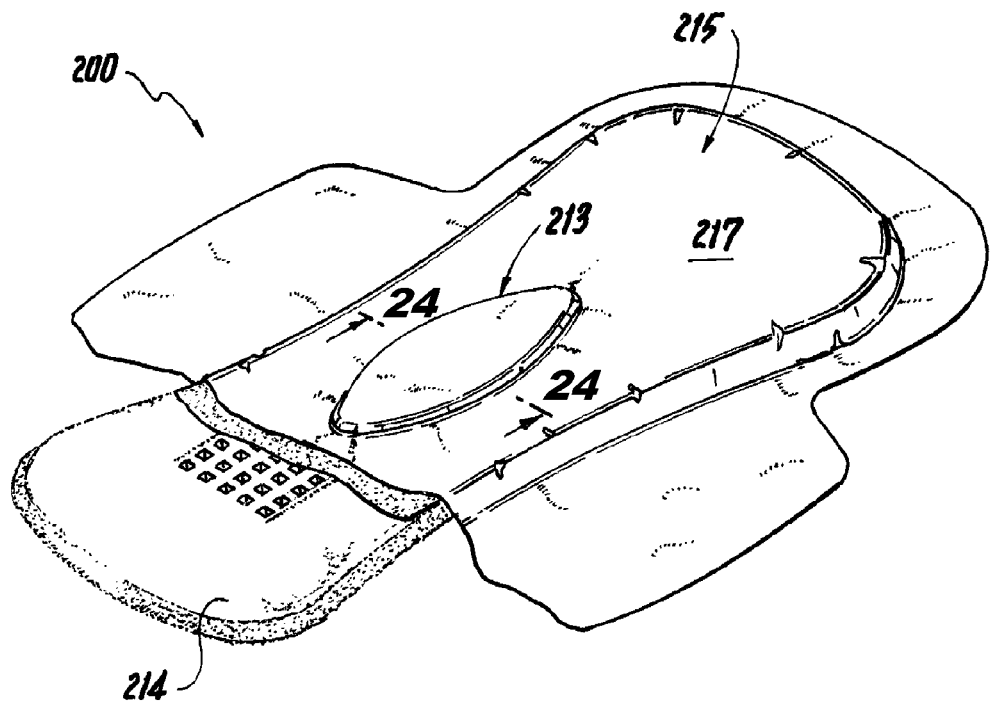
FIG. 23 is a perspective view of an absorbent article according to the present invention with the cover layer and transfer layer thereof partially broken away.
Figure 24:
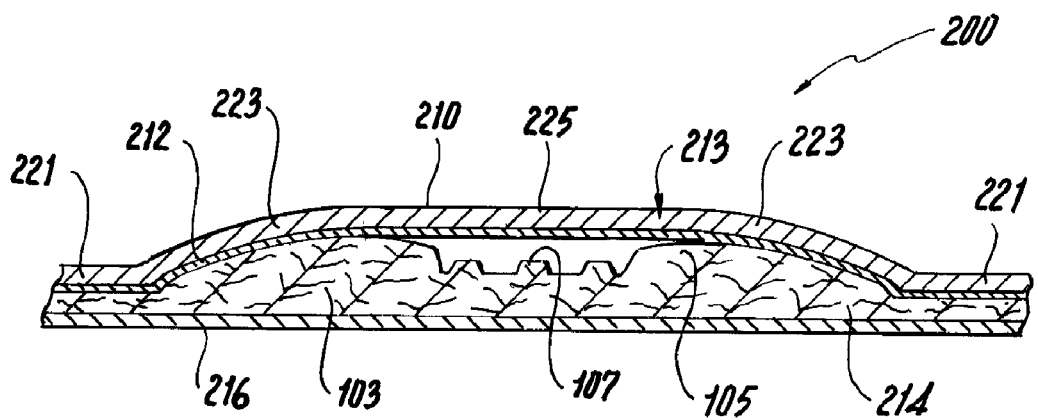
FIG. 24 is a sectional view taken along line 24-24 in FIG. 23.

Reference is made to FIGS. 23-24 which depict a disposable absorbent article 200 in accordance with the present invention. Although disposable absorbent articles according to the present invention will be described herein with reference to a sanitary napkin 200, other disposable absorbent articles such as panty liners, adult incontinence articles, and diapers are considered within the scope of the present invention. As shown in FIG. 24, the sanitary napkin 200 includes a liquid permeable cover layer 210, an optional transfer layer 212, an absorbent core 214 and a liquid impermeable barrier layer 216. The absorbent core 214 layer is formed from a formed fibrous article 12 of the type described above.

As shown in FIG. 23, the absorbent article 200 includes a raised area 213 that extends upwardly from the remaining body facing planar portion 215 of the napkin 200. Specifically the raised area 213 extends upwardly from a top surface 217 of the planar portion 215. Preferably, the raised area 213 extends upwardly a distance of about 2 mm to about 10 mm as measured from the top surface 217 of the planar portion 215 and extends over a surface area of between about 1000 mm$^2$ and 7000 mm². Preferably, the planar portion 215 extends over an area of between about 7000 mm² and 14000 mm².

Main Body—Cover Layer

The cover layer 210 may be a relatively low density, bulky, high-loft non-woven web material. The cover layer 210 may be composed of only one type of fiber, such as polyester or polypropylene or it may include a mixture of more than one fiber. The cover may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. Preferably, the cover layer 210 has a basis weight in the range of about 10 gsm to about 75 gsm.

Bi-component fibers may be made up of a polyester layer and a polyethylene sheath. The use of appropriate bi-component materials results in a fusible non-woven fabric. Examples of such fusible fabrics are described in U.S. Pat. No. 4,555,430 issued Nov. 26, 1985 to Chicopee. Using a fusible fabric increases the ease with which the cover layer may be mounted to the absorbent layer(s) of the article and/or to the barrier layer 216.

The cover layer 210 preferably has a relatively high degree of wettability, although the individual fibers comprising the cover may not be particularly hydrophilic. The cover material should also contain a great number of relatively large pores. This is because the cover layer 210 is intended to take-up body fluid rapidly and transports it away from the body and the point of deposition. Therefore, the cover layer contributes little to the time taken for the napkin 200 to absorb a given quantity of liquid (penetration time).

Advantageously, the fibers that make up the cover layer 210 should not lose there physical properties when they are wetted, in other words they should not collapse or lose their resiliency when subjected to water or body fluid. The cover layer 210 may be treated to allow fluid to pass through it readily. The cover layer 210 also functions to transfer the fluid quickly to the underlying layers of the absorbent article. Thus, the cover layer 210 is advantageously wettable, hydrophilic and porous. When composed of synthetic hydrophobic fibers such as polyester or bi-component fibers, the cover layer 210 may be treated with a surfactant to impart the desired degree of wettability.

In one preferred embodiment of the invention the cover layer 210 is made from a 27 gsm hot through air (HTA) bonded nonwoven material constructed from 100% bico fibers (PE/PET), commercially available from Shalag Industries A.C.S. Ltd., Kibbutz Shamir, Upper Galilee, Israel, under the commercial code STA4ETW27.

Alternatively, the cover layer 210 can also be made of a polymer film having large pores. Because of such high porosity, the film accomplishes the function of quickly transferring body fluid to the underlying layers of the absorbent article. A suitable cover material of this type is commercially found on the Stayfree Dry Max Ultrathin product distributed by McNeil-PPC, Inc.

The cover layer 210 may be embossed to the underlying absorbent layers in order to aid in promoting hydrophilicity by fusing the cover to the adjacent underlying layer. Such fusion may be effected locally, at a plurality of sites or over the entire contact surface of cover layer 210. Alternatively, the cover layer 210 may be attached to the other layers of the article by other means such as by adhesion.

Main Body—Transfer Layer

Adjacent to the cover layer 210 on its inner side and bonded to the cover layer 210 is the optional transfer layer 212. The transfer layer 212 provides means for receiving body fluid from the cover layer 210 and holding it until the underlying absorbent core 214 has an opportunity to absorb the fluid, and therefore acts as a fluid transfer or acquisition layer. The transfer layer 212 is, preferably, more dense than and has a larger proportion of smaller pores than the cover layer 210. These attributes allow the transfer layer 212 to contain body fluid and hold it away from the outer side of the cover layer 210, thereby preventing the fluid from rewetting the cover layer 210 and its surface. However, the transfer layer is, preferably, not so dense as to prevent the passage of the fluid through the layer 212 into the underlying absorbent core 214.

The transfer layer 212 may be composed of fibrous materials, such as wood pulp, polyester, rayon, flexible foam, or the like, or combinations thereof. The transfer layer 212 may also comprise thermoplastic fibers for the purpose of stabilizing the layer and maintaining its structural integrity. The transfer layer 212 may be treated with surfactant on one or both sides in order to increase its wettability, although generally the transfer layer 212 is relatively hydrophilic and may not require treatment. The transfer layer 212 is preferably bonded or adhered on both sides to the adjacent layers, i.e. the cover layer 210 and the underlying absorbent core 214.

Examples of suitable materials for the transfer layer 212 are through air bonded pulp sold by Buckeye Technologies of Memphis, Tenn., under the designation VIZORB 3008, which has a basis weight of 110 gsm, VIZORB 3042, which has a basis weight of 100 gsm, and VIZORB 3010, which has a basis weight of 90 gsm.

Main Body—Absorbent Core

Referring to FIG. 18, and as discussed above, the absorbent article 200 according to the present invention includes an absorbent core 214. The absorbent core 214 consists of a formed fibrous article 12 of the type described herein above.

In one preferred embodiment of the invention, the absorbent core 214 is a blend or mixture of cellulosic fibers and superabsorbent disposed therein. Cellulosic fibers that can be used in the absorbent core 214 are well known in the art and include wood pulp, cotton, flax and peat moss. Wood pulp is preferred.

The absorbent core 214 can contain any superabsorbent polymer (SAP), which are well known in the art. For the purposes of the present invention, the term "superabsorbent polymer" (or "SAP") refers to materials, which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. of Osaka, Japan, under the designation of SA70N and products offered by Stockhausen Inc.

The absorbent core 214 preferably has a total basis weight in the range of about 200 gsm to about 400 gsm. In preferred embodiments of the present invention the absorbent core 214 includes about 50%-100% pulp by weight and about 0% to about 50% superabsorbent by weight.

As described above in the description of the method of making the fibrous article 12 set forth above, and in reference to FIGS. 21 and 22, the absorbent core 214 generally includes an area 101 that has not been pin embossed, a first arcuate raised area 103, a second arcuate raised area 105, a pin embossed region 107 located between the raised area 103 and raised area 105, and a centrally extending pin embossed area 109. Referring to FIG. 24, it is noted that the region 107 located between the raised areas 103 and 105 is recessed related to the raised areas. That is, raised areas 103 and 105 have a greater thickness than region 107.

Figure 25:
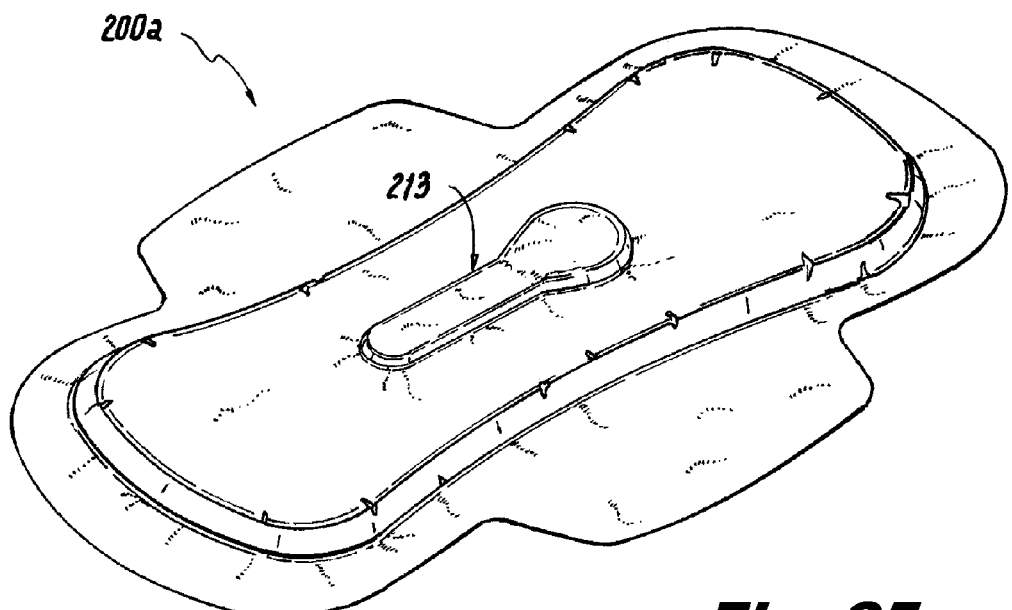
FIGS. 25-26 are perspective views of alternate embodiments of absorbent articles according to the present invention.
Figure 26:
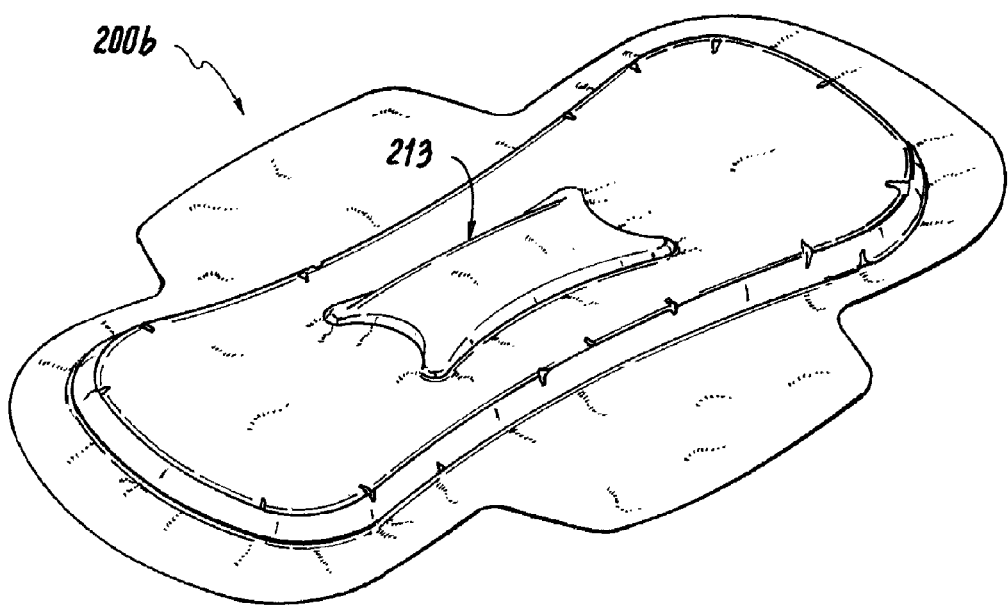

As shown in FIG. 24, the first arcuate raised area 103 and the second arcuate raised area 105 of the absorbent core 214 correspond in location, and help define, the raised area 213 of the napkin 200. However, it is noted that the final shape of the raised area 213 of the napkin 200 is provided by a conventional embossing step (not shown in the figures) and thus the shape of the raised area 213 is not dictated solely by the shape of the first arcuate raised area 103 and the second arcuate raised area 105. The raised area 213 of the napkin 200 may be formed to have any number of different shapes. For example, two alternate embodiments of the napkin 200a and 200b are depicted in FIGS. 25 and 26. As shown, napkins 200a and 200b include raised areas 213 having different shapes than the napkin 200 shown in FIGS. 23 and 24. Other shapes are also possible. In addition, although the napkin 200 is depicted as having only a single raised area 213 is possible that the napkin could be provided with a plurality of such raised areas 213.

All of the articles shown in FIGS. 23-26 use absorbent cores having raised areas 103 and 105 as shown in FIG. 21, and the final shape of the raised area 213 has been modified merely by using a correspondingly shaped conventional embossing roll to emboss the napkin 200 after the various layers of the napkin 200 have been adhered to one another.

Referring to FIG. 24, it is noted that the cover layer extends over the first arcuate raised area 103, the second arcuate raised area 105, as well as the region 107 located between the raised area 103 and raised area 105. In this manner, the cover layer 210 generally includes a first portion 221 which is located in body facing planar portion 215 of the napkin 200 and is arranged in abutting surface to surface contact with the transfer layer 212 (or the absorbent core 214 if the transfer layer 212 is omitted), a pair of second regions 223 that are arranged in corresponding location to the arcuate raised areas 103 and 105 of the absorbent core 214, and a third region 225 that is located between the arcuate raised areas 103 and 105 and is arranged in spaced relationship to the absorbent core 214.

In one specific example of the invention, the absorbent core 214 consists of a 305 gsm fluff pulp and superabsorbent mixture, the mixture including about 89% fluff pulp by weight, commercially available as Golden Isles Fluff Pulp 420#HD 7% Moisture, from GP Cellulose, Brunswick, Ga., USA, and 11% superabsorbent polymer by weight, commercially available as Aqua Keep SA70N from Sumitomo Seika Chemicals Co., Ltd., Osaka, Japan.

Main Body-Barrier Layer

Underlying the absorbent core 214 is a barrier layer 216 comprising liquid-impervious film material so as to prevent liquid that is entrapped in the absorbent core 214 from egressing the sanitary napkin 200 and staining the wearer's undergarment. The barrier layer 216 is preferably made of polymeric film, although it may be made of liquid impervious, air-permeable material such as repellent-treated non-woven or micropore films or foams.

The barrier layer may be breathable, i.e., permits vapor to transpire. Known materials for this purpose include non-woven materials and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet. The cover layer 210 and the barrier layer 216 are joined along their marginal portions so as to form an enclosure or flange seal that maintains the absorbent core 214 captive. The joint may be made by means of adhesives, heat-bonding, ultrasonic bonding, radio frequency sealing, mechanical crimping, and the like and combinations thereof.

In one specific example of the invention, the barrier layer consists of a liquid impermeable 24 gsm polyethylene film commercially available from Clopay do Brasil, Sau Paulo, SP, Brazil.

Positioning adhesive may be applied to a garment facing side of the barrier layer 216 for securing the napkin 200 to the garment during use. The positioning adhesive may be covered with removable release paper so that the positioning adhesive is covered by the removable release paper prior to use.

Absorbent articles of this invention may or may not include wings, flaps or tabs for securing the absorbent article to an undergarment. Wings, also called, among other things, flaps or tabs, and their use in sanitary protection articles is described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly.

The sanitary napkin 200 of the present invention may be applied to the crotch by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to Polystyrene, Polyalpha-methylstyrene, Polyvinyltoluene, and combinations thereof. Suitable Block B poly(monoalkenyl) blocks include, but are not limited to conjugated diene elastomers such as for example polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a co-monomers, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

Any or all of the cover layer 210, transfer layer 212, absorbent core 214, barrier layer 216, and adhesive layers may be colored. Such coloring includes, but is not limited to, white, black, red, yellow, blue, orange, green, violet, and mixtures thereof. Color may be imparted according to the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like. Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

The sanitary napkin 200 may include other known materials, layers, and additives, such as, foam, net-like materials, perfumes, medicaments or pharmaceutical agents, moisturizers, odor control agents, and the like. The sanitary napkin 200 can optionally be embossed with decorative designs.

The sanitary napkin 200 may be packaged as unwrapped absorbent articles within a carton, box or bag. The consumer withdraws the ready-to-use article as needed. The sanitary napkin 200 may also be individually packaged (each absorbent article encased within an overwrap).

Also contemplated by the present invention are asymmetrical and symmetrical absorbent articles having parallel longitudinal edges, dog bone- or peanut-shaped, as well as articles having a tapered construction for use with thong-style undergarments.

From the foregoing description, one skilled in the art can ascertain the essential characteristics of this invention, and without departing from the spirit and scope thereof, can make various changes and modifications. Embodiments set forth by way of illustration are not intended as limitations on the variations possible in practicing the present invention.

EXAMPLES

Specific inventive examples of the present invention, and comparative examples, are described below.

Inventive Example #1

An example of a sanitary napkin according to the invention was constructed as follows. The body facing cover layer was constructed from a 27 gsm hot through air (HTA) bonded nonwoven material constructed from 100% bico fibers (PE/PET), commercially available from Shalag Industries A.C.S. Ltd., Kibbutz Shamir, Upper Galilee, Israel, under the commercial code STA4ETW27.

A 305 gsm formed fibrous absorbent core was arranged below the cover layer and was formed by the process described herein above with reference to FIGS. 1-21. The absorbent core had a composition of 89% by weight of pulp and 11% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan.

As described above with reference to FIGS. 21-22, the absorbent core (i.e. the formed fibrous article 12) was formed to include an area 101 that was not been pin embossed, a first arcuate raised area 103, a second arcuate raised area 105, a pin embossed region 107 located between the raised area 103 and raised area 105, and a centrally extending pin embossed area 109 extending along the longitudinally extending central axis of the article 12, as shown in FIG. 21.

Area 101 had a thickness in the range of about 2 mm, a density of about 0.1 g/cc, and extended over a surface area of 6500 $mm^2$.

Area 103 and 105 each had a thickness of 5 mm and a density of about 0.05 g/cc. Each area 103 and 105 extended over a surface area of 557 $mm^2$.

Area 107 had a thickness of 0.2 mm and a density of 0.5 g/cc in those areas 111 embossed by the pins 78 and a density of 0.3 g/cc and a thickness of 1 mm in those areas outside of areas 111. Area 107 extended over a surface area of 504 $mm^2$.

Area 109 had a thickness of 0.2 mm and a density of 0.5 g/cc in those areas 111 embossed by the pins 78 and a thickness of 1 mm and a density of 0.3 g/cc in those areas outside of areas 111. Area 109 extended over a surface area of 4300 $mm^2$.

A barrier layer was arranged below the core and was formed from a 24 gsm polyethylene film commercially available from Clopay do Brasil, Sao Paulo, SP, Brazil.

Each of the layers of the sanitary napkin were adhered to one another using a conventional hot melt adhesive. After each of the layers were adhered to one another the sanitary napkin was passed through a conventional embossing process to form a raised area of the type shown in FIG. 23. Thus, the sanitary napkin included a planar portion 215 and a raised area 213 extending upwardly form the planar portion 215 as depicted in FIG. 23. The planar portion 215 extended over an area of 13000 $mm^2$ and the raised area 213 extended over an area of 2000 $mm^2$. The sanitary napkin had a thickness of 2.2 mm in the planar portion 215 and a thickness of 4.7 mm in the raised area 213.

Inventive Example #2

An example of a sanitary napkin according to the invention was constructed as follows. The body facing cover layer was constructed from a 27 gsm hot through air (HTA) bonded nonwoven material constructed from 100% bico fibers (PE/PET), commercially available from Shalag Industries A.C.S. Ltd., Kibbutz Shamir, Upper Galilee, Israel, under the commercial code STA4ETW27.

A 305 gsm formed fibrous absorbent core was arranged below the cover layer and was formed by the process described herein above with reference to FIGS. 1-21. The absorbent core had a composition of 89% by weight of pulp and 11% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan.

As described above with reference to FIGS. 21-22, the absorbent core (i.e. the fibrous article 12) was formed to include an area 101 that was not been pin embossed, a first arcuate raised area 103, a second arcuate raised area 105, a pin embossed region 107 located between the raised area 103 and raised area 105, and a centrally extending pin embossed area 109 extending along the longitudinally extending central axis 13 of the article 12, as shown in FIG. 21.

Area 101 had a thickness in the range of about 3 mm, a density of about 0.09 g/cc, and extended over a surface area of 6500 mm².

Area 103 and 105 each had a thickness of 6 mm and a density of about 0.04 g/cc. Each area 103 and 105 extended over a surface area of 557 mm².

Area 107 had a thickness of 0.2 mm and a density of 0.5 g/cc in those areas 111 embossed by the pins 78 and a density of 0.3 g/cc and a thickness of 1 mm in those areas outside of areas 111. Area 107 extended over a surface area of 504 mm².

Area 109 had a thickness of 0.2 mm and a density of 0.5 g/cc in those areas 111 embossed by the pins 78 and a thickness of 1 mm and a density of 0.3 g/cc in those areas outside of areas 111. Area 109 extended over a surface area of 4300 mm².

Each of the layers of the sanitary napkin were adhered to one another using a conventional hot melt adhesive. After each of the layers were adhered to one another the sanitary napkin was passed through a conventional embossing process to form a raised area of the type shown in FIG. 23. Thus, the sanitary napkin included a planar portion 215 and a raised area 213 extending upwardly form the planar portion 215 as depicted in FIG. 23. The planar portion 215 extended over an area of 13000 mm² and the raised area 213 extended over an area of 2000 mm². The sanitary napkin had a thickness of 3.3 mm in the planar portion 215 and a thickness of 5.8 mm in the raised area 213.

Comparative Example #1

A comparative example, representative of the prior art, was construed as follows. The body facing cover layer was constructed from a 27 gsm hot through air (HTA) bonded nonwoven material constructed from 100% bico fibers (PE/PET), commercially available from Shalag Industries A.C.S. Ltd., Kibbutz Shamir, Upper Galilee, Israel, under the commercial code STA4ETW27.

A 305 gsm fibrous absorbent core was arranged below the cover layer. The absorbent core had a composition of 89% by weight of pulp and 11% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan. The absorbent core has a uniform thickness along its length of 2.2 mm and a uniform density along its length of 0.1 g/cc.

Comparative Example #2

A comparative example, representative of the prior art, was construed as follows. The body facing cover layer was constructed from a 27 gsm hot through air (HTA) bonded nonwoven material constructed from 100% bico fibers (PE/PET), commercially available from Shalag Industries A.C.S. Ltd., Kibbutz Shamir, Upper Galilee, Israel, under the commercial code STA4ETW27.

A 305 gsm fibrous absorbent core was arranged below the cover layer. The absorbent core had a composition of 89% by weight of pulp and 11% by weight of superabsorbent polymer. The pulp was Golden Isles Fluff Pulp 420#HD 7% Moisture, commercially available from GP Cellulose, Brunswick, Ga., USA. The superabsorbent polymer was Aqua Keep SA70N commercially available from Sumitomo Seika Chemicals Co., Ltd., Osaka, Japan. The absorbent core has a uniform thickness along its length of 3.3 mm and a uniform density along its length of 0.09 g/cc.

Test Procedures

Absorbent articles according to the present invention provide superior fluid handling characteristics. A number of test procedures are described below that highlight the fluid handling properties of absorbent articles according to the present invention. Prior to conducting any of the described test procedures described below the test product samples should be conditioned for two hours at 21+/−1° C. and 50+/−2% humidity.

Procedure for Measuring Fluid Penetration Time

Fluid Penetration Time is measured by placing a product sample to be tested under a Fluid Penetration Test orifice plate. The orifice plate consists of a 7.6 cm×25.4 cm plate of 1.3 cm thick polycarbonate with an elliptical orifice in its center. The elliptical orifice measures 3.8 cm along its major axis and 1.9 cm along its minor axis. The orifice plate is arranged such that the center of the orifice is aligned with the intersection of the longitudinal and transverse axis of the article, i.e. at the center of the article.

Test fluid was made of the following mixture to simulate bodily fluids:

49.5% of 0.9% sodium chloride solution (VWR catalog #VW 3257-7), 49.05% Glycerin (Emery 917), 1% Phenoxyethanol (Clariant Corporation Phenoxetol™) and 0.45% Sodium Chloride (Baker sodium chloride crystal #9624-05).

A graduated 10 cc syringe containing 7 ml of test fluid is held over the orifice plate such that the exit of the syringe is approximately 3 inches above the orifice. The syringe is held horizontally, parallel to the surface of the test plate. The fluid is then expelled from the syringe at a rate that allows the fluid to flow in a stream vertical to the test plate into the orifice and a stop watch is started when the fluid first touches the sample to be tested. The stop watch is stopped when a portion of the surface of the sample first becomes visible above the remaining fluid within the orifice. The elapsed time on the stop watch is the Fluid Penetration Time. The average Fluid Penetration Time (FPT) is calculated from taking the average of readings from three product samples.

Procedure for Measuring Rewet Potential

The three product samples used for the Fluid Penetration Time (FPT) procedure described above are used for the Rewet Potential test described below.

The rewet potential is a measure of the ability of a napkin or other article to hold liquid within its structure when the napkin contains a relatively large quantity of liquid and is subjected to external mechanical pressure. The rewet potential is determined and defined by the following procedure.

The apparatus for the Rewet Potential test is the same as that set forth above with regard to the FPT test and further includes a quantity of 3 inch×4 (7.62 cm×10.16 cm) inch rectangles of Whatman #1 filter paper from (Whatman Inc., Clifton, N.J.) and a weighing machine or balance capable of weighing to an accuracy of +/−0.001 g, a quantity of said Whatman paper, a standard weight of 2.22 kg (4.8 pounds) having dimensions 5.1 cm (2 inches) by 10.2 cm (4.0 inches) by approximately 5.4 cm (2.13 inches) which applies a pressure of 4.14 kPa (0.6 psi) over the 5.1 by 10.2 cm (2 inches by 4 inches) surface.

For purposes of the test procedure set forth herein, the same three product samples used for the fluid penetration test should be used for the rewet potential test. After the test fluid is applied within the orifice plate in the FPT test described above, and as soon as the cover layer of the napkin first appears through the top surface of the fluid, the stop watch is started and an interval of 5 minutes is measured.

After 5 minutes have elapsed, the orifice plate is removed and the napkin is positioned on a hard level surface with the cover layer facing upwards.

A fifteen (15) layer stack of the pre-weighed filter paper is placed on and centered over the wetted area and the standard 2.22 kg weight is placed on top of the filter paper. The filter paper and the weight are arranged over the absorbent article such that they are centered over the area to which the fluid was applied. The filter paper and the weight are arranged such that their longer dimensions are aligned with the longitudinal direction of the product. Immediately after placing the paper and weight on the product, the stopwatch is started and after a 3 minute interval has elapsed the standard weight and filter paper are quickly removed. The wet weight of the filter paper is measured and recorded to the nearest 0.001 grams. The rewet value is then calculated as the difference in grams between the weight of the wet 15 layers of filter paper and the dry 15 layers of filter paper. The average Rewet Potential is calculated from taking the average of readings from three product samples.

Procedure for Measuring the Thickness of a Sanitary Article

The apparatus required to measure the thickness of the sanitary napkin is a footed dial (thickness) gauge with stand, available from Ames, with a 2" (5.08 cm) diameter foot at a pressure of 0.07 psig (4.826 hPa) and a readout accurate to 0.001" (0.0254 mm). A digital type apparatus is preferred. If the sanitary napkin sample is individually folded and wrapped, the sample is unwrapped and carefully flattened by hand. The release paper is removed from the product sample and it is repositioned back gently across the positioning adhesive lines so as not to compress the sample, ensuring that the release paper lies flat across the sample. Flaps (if any) are not considered when taking the thickness reading.

The foot of the gauge is raised and the product sample is placed on the anvil such that the foot of the gauge is approximately centered on the location of interest on the product sample. When lowering the foot, care must be taken to prevent the foot dropping onto the product sample or undue force being applied. A load of 0.07 psig (4.826 hPa) is applied to the sample and the read out is allowed to stabilize for approximately 5 seconds. The thickness reading is then taken. This procedure is repeated for three product samples and the average thickness is then calculated.

The measured Fluid Penetration Time, Rewet Potential and Product Thickness of the Inventive Examples and Comparative Examples described above are summarized in the table set forth below.

|  | Thickness in Raised Area (mm) | Thickness in Planar Portion (mm) | Fluid Penetration Time (s) | Rewet (g) |
| --- | --- | --- | --- | --- |
| Inventive Example #1 | 4.7 | 2.2 | 17 | 0.98 |
| Inventive Example #2 | 5.8 | 3.3 | 11 | 0.96 |
| Comparative Example #1 | NA | 2.2 | 52 | 0.82 |
| Comparative Example #2 | NA | 3.3 | 25 | 1.43 |

As shown above, disposable absorbent articles according to the present provide superior fluid handling characteristics.

We claim:

1. An apparatus for making a formed fibrous article having a three dimensional profile, the apparatus comprising:

a calendering station including a first roll and a second roll, wherein the second roll includes at least one recess for providing a formed fibrous article with a three dimensional profile;

a pin calendering station comprising a first roll and a second roll, wherein the first roll and second roll are structured and arranged to convey a fibrous article through a nip defined between the first and second roll without the use of a carrier layer.

2. The apparatus according to claim 1, wherein the first roll of the calendering station comprises a vacuum roll and the second roll comprises an opposed calender roll.

3. The apparatus according to claim 2, wherein the recess extends over an area in the range of about 500 mm$^2$ to about 5000 mm$^2$.

4. The apparatus according to claim 3, wherein the recess has a depth in the range of about 2 mm to 25 mm as measured from a surface of the calender roll located outside of the recess.

5. The apparatus according to claim 4, wherein the recess has a maximum width in the range of about 20 mm to 120 mm as measured in a machine direction and a maximum width as measured in a transverse direction in the range of about 5 mm to about 60 mm.

6. The apparatus according to claim 2, wherein the first roll of the pin calendering station comprises a vacuum roll and the second roll comprises a pin calender roll.

7. The apparatus according to claim 6, wherein the vacuum roll of the pin calendering station includes a rotatable cylinder and a plurality of holes extending through a surface of the cylinder and the pin calender roll includes a plurality of pins extending outwardly from a surface of the pin calender roll.

8. The apparatus according to claim 7, wherein each one of the plurality of pins is arranged such that it does not overlap with any of the plurality of holes.

9. The apparatus according to claim 8, wherein the pin calender roll includes a first area having a plurality of the plurality of pins, the first area extending down a central portion of the roll surface.

10. The apparatus according to claim 9, wherein the pin calender roll includes a first recess, a second recess, and a land area located between the first and second recess, the land area including a plurality of the plurality of pins.

11. The apparatus according to claim 2, further comprising a chamber for holding fibrous pulp.

12. The apparatus according to claim 11, further comprising a forming drum in communication with the chamber, wherein the forming drum including a rotatable cylinder having a plurality of molds mounted thereto.

13. The apparatus according to claim 12, further comprising a vacuum chamber arranged within the rotatable cylinder, the vacuum chamber being structured and arranged to sequentially draw the fibrous pulp into each one of the plurality of molds.

14. The apparatus according to claim 13, wherein the vacuum roll of the calendering station includes a rotatable cylinder having a plurality of holes extending through a surface of the rotatable cylinder.

15. The apparatus according to claim 14, further comprising a vacuum chamber arranged within the rotatable cylinder of the calendering station, the vacuum chamber arranged within the rotatable cylinder adapted to draw air through the plurality of holes in the rotatable cylinder.

16. The apparatus according to claim 15, wherein a leading edge of the vacuum chamber arranged within the rotatable cylinder of the calendering station is substantially aligned with a trailing edge of the vacuum chamber located with the rotatable cylinder of the forming drum, the arrangement of the vacuum chambers being adapted to transfer the fibrous article from the forming drum to the vacuum roll of the calendering station.

17. The apparatus according to claim 16, wherein the vacuum roll of the pin calendering station includes a vacuum chamber arranged within the rotatable cylinder of the vacuum roll.

18. The apparatus according to claim 17, wherein the vacuum chamber arranged within the rotatable cylinder of the pin calendering station is arranged so that a leading edge of the vacuum chamber is substantially aligned with a trailing edge of the vacuum chamber located within the rotatable cylinder of the vacuum roll in the calendering station.

19. The apparatus according to claim 18, further comprising a transfer wheel arranged operative relationship with the pin calendering station.

20. The apparatus according to claim 19, wherein the transfer wheel comprises a vacuum roll and a porous conveyor belt.

21. The apparatus according to claim 20, wherein the vacuum roll of the transfer wheel includes a rotatable cylinder and a vacuum chamber arranged within the rotatable cylinder.

22. The apparatus according to claim 21, wherein the porous conveyor belt extends around the rotatable cylinder of the transfer wheel.

23. The apparatus according to claim 22, wherein the vacuum chamber arranged within the rotatable cylinder of the transfer wheel is arranged so that a leading edge of the vacuum chamber arranged within the rotatable cylinder of the transfer wheel is substantially aligned with a trailing edge of the vacuum chamber located within the rotatable cylinder of the vacuum roll in the pin calendering station.

* * * * *